United States Patent [19]
Korsmeyer et al.

[11] Patent Number: 6,165,732
[45] Date of Patent: *Dec. 26, 2000

[54] METHOD FOR IDENTIFYING APOPTOSIS MODULATING COMPOUNDS

[75] Inventors: Stanley J. Korsmeyer, Clayton; Paul H. Schlesinger, St. Louis, both of Mo.

[73] Assignee: Washington University, St. Louis, Mo.

[ * ] Notice: This patent issued on a continued prosecution application filed under 37 CFR 1.53(d), and is subject to the twenty year patent term provisions of 35 U.S.C. 154(a)(2).

[21] Appl. No.: 09/127,048

[22] Filed: Jul. 31, 1998

Related U.S. Application Data

[60] Provisional application No. 60/061,823, Oct. 14, 1997.

[51] Int. Cl.[7] .............................. G01N 33/50; C07K 2/00
[52] U.S. Cl. .................. 435/7.2; 435/7.21; 435/7.23; 530/350
[58] Field of Search .................................. 424/9.1, 9.321; 435/4, 7.2, 7.21, 7.23; 530/350; 536/23.1, 23.5

[56] References Cited

FOREIGN PATENT DOCUMENTS

WO96/35951 11/1996 WIPO.

OTHER PUBLICATIONS

Patent Cooperation Treaty International Search Report for PCT/US99/17276, Mar. 2, 2000.

Gross et al., EMBO Journal, vol. 17, No. 14, pp. 3878–3885, XP002130759, Enforced dimerization of BAX results in its translocation, Jul. 15, 1998.

Jurgensmeier et al., Proc. of the Nat. Acad. of Sci. of the U.S.A., vol. 95, No. 9, pp. 4997–5002, XP002130758, *Bax directly induces release of cytochrome c from isolated mitochondria*, Apr. 28, 1998.

Antonsson et al., Inhibition of Bax Channel–Forming Activity by Bcl–2, *Science* 277:370–372 (1997).

Gajewski et al., Apoptosis Meets Signal Transduction: Elimination of a BAD Influence, *Cell* 87:589–592 (1996).

Minn et al., Bcl–$x_L$ forms an ion channel in synthetic lipid membranes, *Nature* 385:353–357 (1997).

Muchmore et al. X–ray and NMR structure of human Bcl–$x_L$, an inhibitor of programmed cell death, *Nature* 381:335–341 (1996).

Schendel et al., Channel formation by antiapoptotic protein Bcl–2, *PNAS USA* 94, 5113 (1997).

*Primary Examiner*—Donna C. Wortman
*Assistant Examiner*—Brenda G. Brumback
*Attorney, Agent, or Firm*—Howell & Haferkamp, LC

[57] ABSTRACT

Methods for identifying apoptosis-modulating compounds using lipid bilayers are provided. One method involves contacting a compound of interest with a lipid bilayer which contains an ion-channel formed by an anti-apoptotic or pro-apoptotic polypeptide of the BCL-2 family and assaying for changes in the ion conductance properties of the channel, including ion selectivity, single channel conductance and rectification. A second method identifies compounds which can form ion channels in planar lipid bilayers and determines the ion selectivity and pH dependence of such channel formation, where apoptosis modulating activity is predicted based on comparing these channel forming characteristics with those of Bcl-2 family members.

10 Claims, 20 Drawing Sheets

|         | α5                          | α6                              | α6          |
|---------|-----------------------------|---------------------------------|-------------|
| Bcl-2 142 | NWGRI VAFFEFGGVMCVESVNREMSPLVDNI | AL WMTEYLNRH- | HTWI QDN   192 |
| Bax 105  | NWGRVVALFYFASKLVLKALCTKVPELI RTI MGWTLDFLRER- | LLGWI QDQG 155 |
| Bak 123  | NWGRVVALLGFGYRLALHVYQHGLTGFLGQVTRFVVDFML HHCI ARWI AQR 174 |
| Bcl-xL 135 | NWGRI VAFFSFGGALCVESVDKEMQVLVSRI AAWMATYLNDH- | LEPWI QEN 185 |

FIGURE 7

BCL-2 slope = 1.08±0.003 ps
pK/pCl = 2.4

BCL-2 + 150 μM 11mer slope (neg potentials) =
1.08±0.022 pS
pK/pCl = 0.26±0.05 slope(neg potentials) =
1.50±0.001 pS
pK/Pcl = 0.32

THE BCL-2 FAMILY

ANTI-APOPTOTIC

MAMMALIAN

Bcl-2
Bcl-x$_L$
Bcl-w
Mcl1
A1
NR-13

*C. elegans*

Ced-9

VIRAL HOMOLOGS

LMW5-HL
BHRF1
KSbcl-2
E1B 19K

PRO-APOPTOTIC

Bax
Bak

PRO-APOPTOTIC — BH3

Bik
Bid
Bad

```
Human Bax    MDGSGE- · · · · · · · · · · · · · · · · · · · · · · · · · · · · · · · · · · · · QPRGGGPTSSEQI MKTGALL        26
Mouse Bax    MDGSGE- · · · · · · · · · · · · · · · · · · · · · · · · · · · · · · · · · · · · QPRGGGPTSSEQI MKTGALL        26
Human Bcl-2  MAHAGRSGYDNREI VNKYI HYKLSQRGYEWDAGDVGAAPPGAAPAPGFFS                                                          50
Mouse Bcl-2  MAQAGRTGYDNREI VMKYI HYKLSQRGYEWDAGDADAAPLGAAPTPGI FS                                                         50

Human Bax    LQGFI QDRAG- · · RMGGEAPELALDPVPQDASTKKLSEC- · · · · · · LKRI                                                 66
Mouse Bax    LQGFI QDRAG- · · RMGGEAPELALDPVPQDASTKKLSEC- · · · · · · LKRI                                                 66
Human Bcl-2  SQPGHTPHPAASRDPVARTSPLQTPAAPGAAAGPALSPVPPVVHLTLRQA                                                            100
Mouse Bcl-2  FQPESNPMPAVHREMAARTSPLRPLVA- · · TAGPALSPVPPCVHLTLRRA                                                          97

Human Bax    GDELDSN- · · MELQRMI AAVDTDS- · PREVFFRVAADMFSDGNFNWGRVVA                                                     112
Mouse Bax    GDELDSN- · · MELQRMI AAVDTDS- · PREVFFRVAADMFSDGNFNWGRVVA                                                     112
Human Bcl-2  GDDFSRRYRRDFAEMSSQLHLTPFTARGCFATVVEELFRDGVNWGRI VA                                                            149
Mouse Bcl-2  CDDFSRRYRRDFAEMSSQLHLTPFTARGRFATVVEELFRDG- VNWGRI VA                                                          146

Human Bax    LFYFASKLVLKALCTKVPELI RTI MGWTLDFLRERLLGWI QDQGGWDGLL                                                          162
Mouse Bax    LFYFASKLVLKALCTKVPELI RTI MGWTLDFLRERLLGWI QDQGGWDGLL                                                          162
Human Bcl-2  FFEFGGVMCVESVNREMSPLVDNI ALWMTEYLNRHLHTWI QDNGGWDAFV                                                           199
Mouse Bcl-2  FFEFGGVMCVESVNREMSPLVDNI ALWMTEYLNRHLHTWI QDNGGWDAFV                                                           196

Human Bax    SYFGTP- · · · · · · · · TWQTVTI FVAGVLTAS- · · LTI WKKMG                                                      192
Mouse Bax    SYFGTP- · · · · · · · · TWQTVTI FVAGVLTAS- · · LTI WKKMG                                                      192
Human Bcl-2  ELYGPSMRPLFDFSWLSLKTLLSLALVGACI TLGAYLGHK                                                                    239
Mouse Bcl-2  ELYGPSMRPLFDFSWLSLKTLLSLPWGACI TLGAYLGHK                                                                     236
```

FIGURE 11

METHOD FOR IDENTIFYING APOPTOSIS MODULATING COMPOUNDS

CROSS-REFERENCE TO RELATED APPLICATIONS

This application claims the benefit of, and incorporates herein by reference, the U.S. Provisional Application Ser. No. 60/061,823, which was filed on Oct. 14, 1997.

REFERENCE TO GOVERNMENT GRANT

This invention was made with government support under Grant Number ADRC #AG05681-14. The government has certain rights in this invention.

BACKGROUND OF THE INVENTION

(1) Field of the Invention

This invention relates generally to the regulation of apoptosis and to compounds which modulate apoptosis, both antagonists and agonists, and more particularly, to a method for identifying compounds with pro-apoptotic or anti-apoptotic activity.

(2) Description of the Related Art

Programmed cell death, referred to as apoptosis, plays an indispensable role in the development and maintenance of homeostasis within all multicellular organisms (Raff, *Nature* 356:397–400, 1992). Genetic and molecular analysis from nematodes to humans has indicated that the apoptotic pathway of cellular suicide is highly conserved (Hengartner and Horvitz, *Cell* 76:1107–1114, 1994). In addition to being essential for normal development and maintenance, apoptosis is important in the defense against viral infection and in preventing the emergence of cancer.

The BCL-2 family of proteins constitutes an intracellular checkpoint of apoptosis. The founding member of this family is the apoptosis-inhibiting protein encoded by the bcl-2 protooncogene which was initially isolated from a follicular lymphoma (Bakhshi et al., *Cell* 41:889–906, 1985; Tsujimoto et al, *Science* 229:1390–1393, 1985; Cleary and Sklar, *Proc Natl Acad Sci USA* 82:7439–7443, 1985). The Bcl-2 protein is a 25 kD, integral membrane protein localized to intracellular membranes including mitochondria. This factor extends survival in many different cell types by inhibiting apoptosis elicited by a variety of death-inducing stimuli (Korsmeyer, *Blood* 80:879–886, 1992).

The family of BCL-2-related proteins is comprised of both anti-apoptotic and pro-apoptotic members that function in a distal apoptotic pathway common to all multi-cellular organisms. It has been suggested that the ratio of anti-apoptotic (Bcl-2, BCl-$x_L$, Mcl-1 and A1) to pro-apoptotic (Bax, Bak, Bcl-$x_S$, Bad, Bik and Bid) molecules may be involved in determining whether a cell will respond to a proximal apoptotic stimulus. (Oltvai et al., *Cell* 74:609–619, 1992; Farrow, et al., *Curr. Opin. Gen. Dev.* 6: 45–49, 1996). Because members of this family can form both homodimers and heterodimers, the latter often between anti- and pro-apoptotic polypeptides, the balance of these homodimers and heterodimers could play a role in regulating apoptosis (Oltvai and Korsmeyer, *Cell* 79:189–192, 1994).

Members of the BCL-2 family have been defined by sequence homology that is largely based upon conserved motifs termed BCL-Homology domains. (Yin et al, *Nature* 369:321–323, 1994). BCL-Homology domains 1 and 2 (BH1 and BH2) domains have been shown to be important in dimerization and in modulating apoptosis (Yin et al., supra). A third homology region, BH3, has been found in some family members and shown to be important in dimerization as well as promoting apoptosis (Boyd et al., *Oncogene* 11:1921–1928; Chittenden et al., *Embo J* 14:5589–5596, 1995). BH4, the most recently identified homology domain, is present near the amino terminal end of some pro-apoptotic family members (Farrow et al., supra).

All known members of the BCL-2 family other than Bad and Bid have a C-terminal membrane-anchoring tail (TM). BCL-2 family members with a TM are intracellular integral membrane proteins most convincingly localized to mitochondria, the endoplasmic reticulum and the nuclear membrane. The intracellular membrane localization of BCL-2 family members together with the identification of structural similarity between the BCl-$x_L$ monomer and the ion-pore forming toxins of colicin and diphtheria toxin B fragment (Muchmore et al., *Nature* 381:335–341, 1996) has prompted electrophysiological studies by several groups on the ability of BCL-2 family members to form ion channels in artificial lipid membranes.

For example, the anti-apoptotic family members Bcl-$x_L$ and Bcl-2 lacking the TM (Bcl-$x_L\Delta$TM and Bcl-2$\Delta$TM) were shown to insert into synthetic lipid vesicles at pH values below 5.5, but had little or no detectable pore forming activity when added to lipid vesicles at pH values above 5.5 (Minn et al., *Nature* 385:353–356, 1997; Schendel et al., *PNAS USA*:94, 5113, 1997; and Antonsson et al., *Science* 277:370–372, 1997). When added to planar lipid bilayers at physiological pH, Bcl-$x_L\Delta$TM formed channels which exhibit multiple conductance states and which have an ion selectivity sequence of $K^+=Na^+>Ca^{2+}>Cl^-$ (Minn et al., supra). Bcl-2$\Delta$TM also formed a channel in lipid bilayers at physiological pH having multiple channel conductance states, with a primary conductance of 18±2 pS being consistent with pore formation by Bcl-2 homodimers (Schendel et al., supra). Schendel et al reported that the Bcl-2$\Delta$TM channel is cation selective at pH 5.4 but did not test ion selectivity at neutral pH.

In addition, it has been reported that Bax$\Delta$TM had an intrinsic pore-forming activity in liposomes that was antagonized by Bcl-2 at physiological pH (Antonsson et al., supra). This reference also reported that Bax$\Delta$TM formed voltage-dependent channels in planar lipid bilayers at pH 7.0 that were slightly cation selective, with a permeability ratio of $Na^+$ to $Cl^-$ of about 2.1.

These electrophysiological studies have led to speculation that Bcl-2 related proteins may modulate apoptosis by regulating the permeability of intracellular membranes in which they are localized. For example, it has been suggested that both Bcl-2 and Bax may allow transport of an ion or a protein across membranes, but in a cytoprotective or a cytodestructive direction, respectively (Schendel et al., supra). In addition, one group speculated that the development of specific Bax channel blockers may be of therapeutic utility in the treatment of neuronal apoptosis (Antonsson et al., supra).

However, until the work reported herein, no direct cause and effect relationship had been shown for the ion conductance state of a channel formed in synthetic planar lipid bilayers by a BCL-2 family member and the modulation of apoptosis. Moreover, there was no description of how to recognize a candidate death agonist or death antagonist by its affect on the ion conductance state of lipid bilayer channels formed by BCL-2 family members.

Some disease conditions are believed to be related to the development of a defective down-regulation of apoptosis in the affected cells. For example, neoplasias may result, at least in part, from an apoptosis-resistant state in which cell proliferation signals inappropriately exceed cell death signals. Furthermore, some DNA viruses such as Epstein-Barr virus, African swine fever virus and adenovirus, parasitize the host cellular machinery to drive their own replication and at the same time modulate apoptosis to repress cell death and allow the target cell to reproduce the virus. Moreover, certain disease conditions such as lymphoproliferative conditions, cancer including drug resistant cancer, arthritis, inflammation, autoimmune diseases and the like may result from a down regulation of cell death regulation. In such disease conditions it would be desirable to promote apoptotic mechanisms.

Conversely, in other disease conditions it would be desirable to inhibit apoptosis such as in the treatment of immunodeficiency diseases, including AIDS, senescence, neurodegenerative disease, ischemic and reperfusion cell death, infertility, wound-healing, and the like. In the treatment of such diseases it would be desirable to inhibit apoptotic mechanisms.

Thus, it would be desirable to elucidate the biochemical mechanisms involved in the regulation of apoptosis by BCL-2 family members and to utilize these mechanisms as a basis for identifying compounds which promote or inhibit death. Such compounds would be useful in developing treatment regimens for advantageously modulating the apoptotic process in disease conditions involving either inappropriate repression or inappropriate enhancement of cell death.

SUMMARY OF THE INVENTION

Accordingly, the inventors herein have succeeded in discovering (1) that anti-apoptotic and pro-apoptotic BCL-2 family members form channels in artificial membranes that have distinct characteristics, including ion selectivity, conductance, voltage dependence and rectification and (2) that compounds which modulate these characteristics also modulate apoptosis. In particular, fusion of lipid vesicles with incorporated anti-apoptotic Bcl-2 or pro-apoptotic Bax, i.e., proteoliposomes, at neutral pH result in $K^+$-selective or $Cl^-$-selective channels, respectively, with Bcl-2 most often displaying a complex multichannel conductance pattern having no rectification and Bax displaying a simpler single channel conductance pattern having mild rectification. Upon exposure to a Bax 11mer peptide (ECLKRIGDELD) (SEQ ID NO:1) known to induce cell death, Bcl-2 channels acquire characteristics more similar to those of Bax channels, including $Cl^-$ selectivity, a simpler single channel conductance pattern, and rectification.

The relationship between apoptotic activity and ion selectivity is also established by channel forming experiments performed with mutant Bcl-2 and Bax polypeptides having altered apoptotic activity. In particular, a mosaic Bcl-2 polypeptide in which the BH3 domain was substituted with a Bax BH3 domain both promotes cell death and forms a $Cl^-$-selective channel in a planar lipid bilayer. Conversely, a naturally occurring mutant Bax polypeptide which has lost its apoptotic activity forms a $K^+$-selective channel.

Accordingly, one aspect of the present invention provides a method for identifying apoptosis-modulating compounds, which comprises providing a lipid bilayer comprising a channel comprised of a polypeptide from the BCL-2 family, contacting the bilayer with a compound of interest, and determining ion selectivity of the channel. A cell death agonist can be identified by its effect in changing the selectivity of a channel comprised of an anti-apoptotic polypeptide from cation-selective to anion-selective. Alternatively, if the channel comprises a pro-apoptotic polypeptide, a cell death antagonist will change the channel from anion-selective to cation-selective. Anti-apoptotic polypeptides of the BCL-2 family include the mammalian proteins Bcl-2, Bcl-$x_L$, Mcl1, A1, and NR-13, while pro-apoptotic polypeptides of this family include Bax, Bak, Bik, Bid, and Bad (FIG. 10).

In one embodiment, the lipid bilayer comprises a planar bilayer in the presence of an ion concentration gradient and the determining ion selectivity step comprises measuring the reversal potential of the channel. In another embodiment, the lipid bilayer comprises a proteoliposome loaded with a mixture of cations and anions in known amounts and the determining ion selectivity step comprises measuring the relative rates of cation and anion efflux from the proteoliposome using ion specific electrodes.

The channel forming activities of Bcl-2 and Bax are also distinguished by their different responses to pH in mediating release of $Cl^-$ from KCl loaded lipid vesicles. While the same quantities of each protein initiate rapid release of $Cl^-$ (75%) when added at pH 4.0, Bcl-2 is twice as active as Bax at pH 3.5, e.g., Bcl-2 and Bax release 81% and 41% of the $Cl^-$, respectively, but Bax is more active than Bcl-2 at pH 5.0, e.g., releasing 41% of the $Cl^-$ as opposed to 7% released by Bcl-2. The structural basis for this distinction is due to the composition of helices α-5 and α-6 in BCL-2 family members. The acidic content of the α-5 and α-6 helices of Bax and other pro-apoptotic family members define their low pH activity and will always give them an insertion ratio of greater than 1 when comparing insertion in lipid bilayers at low pH and neutral pH values. Conversely, these helices in Bcl-2 and other anti-apoptotic family members are loaded with more of the basic lysine, arginine and histadine residues, which will decrease in polarity with increasing pH. Thus, $Cl^-$ release from liposomes in the presence of an anti-apoptotic BCL-2 family member will not decrease as much with neutral pH.

Thus, another aspect of the invention provides a method for identifying apoptosis-modulating compounds which comprises both evaluating ion selectivity of a channel formed by a test compound and assessing pH dependence of channel formation by the test compound. Evaluating ion selectivity comprises providing a lipid bilayer, contacting the bilayer with a compound of interest, and assaying for ion-selective channel formation. Assessing pH-dependence of channel formation comprises (1) providing lipid vesicles in a solution having a pH of 3.5, pH 4.0, pH 5.0, or pH 7.0, the vesicles containing a channel indicator, (2) contacting the test compound with each of the vesicles, and (3) assaying for release of the channel indicator from the vesicles. If, like Bax, the compound forms an anion-selective channel, shows a ratio of channel indicator release at pH 3.5 and pH 4.0, ($R_{3.5/4.0}$) of less than 1, and shows a ratio of indicator release at pH 4.0 and 5.0 ($R_{4.0/5.0}$) of between 1 and 2, the compound will have apoptotic activity. Conversely, the compound is anti-apoptotic if it behaves like Bcl-2 in these tests, i.e., it forms a cation-selective channel and produces a $R_{3.5/4.0}$ of about 1.0 and a $R_{4.0/5.0}$ of greater than 7.0.

Among the several advantages found to be achieved by the present invention, therefore, may be noted the provision of a novel lipid bilayer-based method for screening compounds for apoptosis-modulating activity that allows compounds to be evaluated without regard to their ability to penetrate into cells or stability in a cell-based assay, the provision of a method that can rapidly screen large numbers of compounds for apoptosis-modulating activity, the provision of death agonists and antagonists identified by this lipid-bilayer screening method, and the use of these compounds for modulating apoptosis.

BRIEF DESCRIPTION OF THE DRAWINGS

FIG. 6 illustrates models of the three-dimensional structure of the α-5 and α-6 helices of Bax (FIG. 6A) and Bcl-2 (FIG. 6B) showing surfaces as colored deep blue for the most positively charged regions and deep red in the most negatively charged regions, with linear interpolation for values in-between;

FIG. 7 illustrates the aligned sequences of α-5 and α-6 helices in two anti-apoptotic (Bcl-$x_L$ and Bcl-2) (SEQ ID NOS:2–3) and in two pro-apoptotic molecules (Bax and Bak) (SEQ ID NOS:4–5);

FIG. 11 illustrates the aligned sequences of mouse and human Bax (SEQ ID NOS:6–7) and human and mouse Bcl-2 (SEQ ID NOS:8–9), with identical residues and conservative substitutions shaded dark and light, respectively, exon boundaries indicated by vertical dashed lines, and the BH1 and BH2 domains boxed.

DESCRIPTION OF THE PREFERRED EMBODIMENTS

Figure 1A:
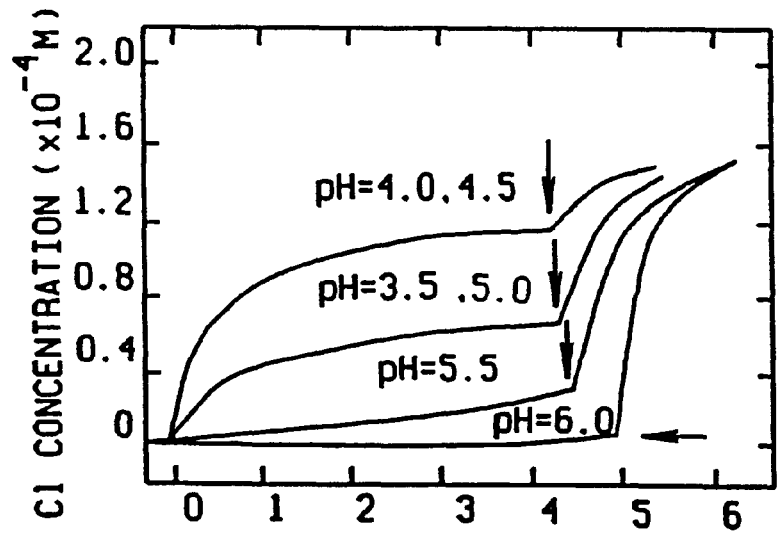
FIG. 1 illustrates the effect of pH on Bax and Bcl-2 induced release of Cl⁻ ions from synthetic lipid vesicles, showing (FIG. 1A) vesicles incubated with BaxΔTM at pH 3.5, 4.0, 4.5, 5.0, 5.5, and 6.0, (FIG. 1B) vesicles incubated with Bcl-2ΔTM at pH 3.5, 4.0, 4.5 and 5.0, (FIG. 1C) vesicles incubated with BaxΔTM at pH 6.0 shifted to pH 4.0 at the time point indicated with the vertical arrow, and (FIG. 1D) vesicles incubated with Bcl-2ΔTM at pH 5.0 shifted to pH 4.0 at the time point indicated with the vertical arrow.

The present invention is based on the surprising discoveries (1) that the ion-selectivity of channels formed by a BCL-2-related polypeptide in synthetic lipid membranes is dependent upon whether the polypeptide has anti-apoptotic activity or pro-apoptotic activity, specifically anti-apoptotic polypeptides are K⁺-selective while pro-apoptotic polypeptides are Cl⁻-selective, and (2) that a compound which modulates this selectivity can modulate apoptosis. These discoveries were unexpected because Bax, which is pro-apoptotic, had previously been reported to be cation selective at pH 7.0 with a permeability ratio of Na⁺ to Cl⁻ of about 2.1 (Antonsson et al., supra) and because no connection had previously been made between ion selectivity of a channel formed by a BCL-2 family member and apoptotic activity.

Therefore, the present invention provides a novel method for identifying apoptosis-modulating compounds which involves assaying the effect of candidate compounds on the ion selectivity of a channel in a lipid bilayer, the channel being comprised of a polypeptide from the BCL-2 family. As used herein, the term compound is intended to include inorganic or organic chemical compounds as well as biochemical molecules such as nucleic acids, proteins, lipids, lipoproteins, and carbohydrates.

The lipid bilayer assay described herein has several advantages over a whole cell assay to identify candidate death agonists and antagonists. First, it provides specific information about the biochemical effect of compounds on what is believed to be an underlying biochemical mechanism of the regulation of apoptosis by BCL-2 family members. As reported herein, it is believed that the pro-apoptotic and anti-apoptotic family members normally form separate ion channels having distinct pro-apoptotic and anti-apoptotic activities and that altering the balance of these activities, such as by enhancing the first activity or reducing the second activity, will initiate apoptosis. In addition, a lipid bilayer assay will identify more candidate death agonists and antagonists than the whole cell assay. For example, some compounds that have apoptotic activity are not detected by the whole cell assay due to cell uptake problems or degradation of the compound by the cell. However, such problems might be overcome in further development or modification of a lead compound identified by a lipid bilayer assay.

The lipid bilayer used in the method comprises a double layer of lipid in a hydrophilic environment. In some embodiments, the lipid bilayer comprises a planar bilayer, while in other embodiments, the lipid bilayer comprises a proteoliposome. Preparation of such lipid bilayers can be accomplished using biochemicals and techniques typically used in bilayer reconstitution experiments. See, e.g., Hanke, W. and Schlue, W.-R., *Planar Lipid Bilayers*, D. B. Sattelle, ed., Academic Press, 1993. The lipids in the bilayer can comprise natural lipids purified from biological membranes and/or synthetic lipids. Examples of natural lipids include but are not limited to Azolectin, a commercially available lipid extract from soybeans (Sigma, St. Louis, Mo.), and phosphatidylcholine and phosphatidylethanolamine purified from egg yolk. Synthetic lipids can be lipids which are pure in their head-group and hydrocarbon composition or lipids that are not normally present in biological membranes. Preferably, the lipid bilayer comprises at least 10% negatively charged lipids. The lipid composition of planar bilayers preferably comprises about 10–20% choline and 80–90% negatively charged lipids. Liposomes preferably comprise about 60% 1,2 dioleoyl phophatidyl choline and about 40% 1,2 dioleoyl phosphatidyl glycerol.

A planar lipid bilayer is established using standard techniques (Hanke and Schlue, supra). In brief, a double compartment chamber with an aperture having a diameter of about 0.1 to about 1 mm and a thickness of about 1 mm or less between the compartments is filled with an aqueous solution to completely cover the aperture. The aqueous solution is typically a KCl solution although other salt solutions can be used, including NaCl and $CaCl_2$. Preferably, the salt solution is comprised of monovalent cations and monovalent anions. A drop of lipid dissolved in an organic nonpolar solvent is then spread across the aperture and allowed to thin to the thickness of a lipid bilayer. The concentration of lipids in the lipid solution is between about 1 and 100 mg/ml, preferably between 20 and 80 mg/ml, and more preferably between 30 and 70 mg/ml. Most preferably, the lipid concentration is 50 mg/ml. Decane is generally used as the solvent, but the solvent can also be other short chain alkanes such as hexane as well as long-chain alkanes and alkenes such as squalene. When the solvent is decane, the lipid bilayer will have a specific capacity of about 0.4 $\mu F/cm_2$. Preferably, the aperture is pretreated with lipid by covering it with the lipid solution and then evaporating the solvent. After pretreatment, the compartments are filled with the aqueous solution and a second drop of lipid solution is spread on the aperture for forming the lipid bilayer.

The planar lipid bilayer can also be prepared by other techniques known in the art such as by forming a folded bilayer across the aperture from two monolayers, one in each compartment, and apposition of two monolayers at the tip of a patch pipet (Hanke and Schlue, supra).

Figure 10:
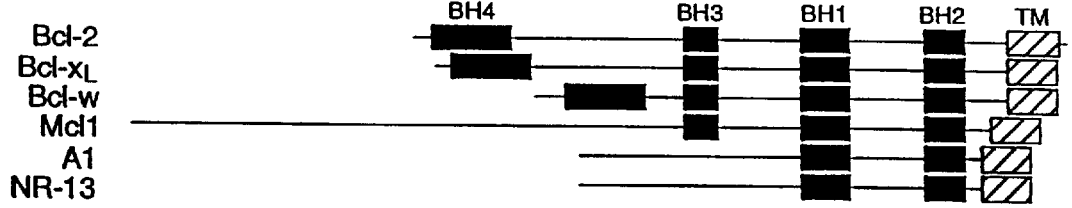
FIG. 10 illustrates the members of the BCL-2 family showing the presence and location of homology domains BH1, BH2, BH3 and BH4, as well as the transmembrane domain (TM)
Figure 10:
Figure 10:
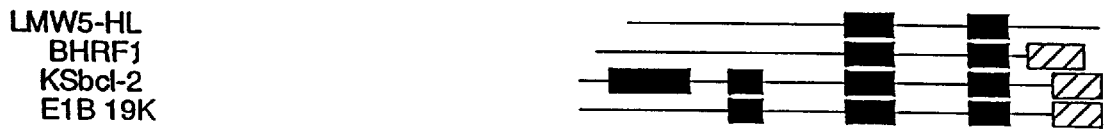
Figure 10:
Figure 10:
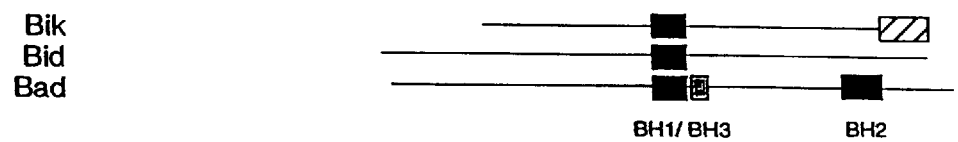

The lipid bilayer comprises at least one channel comprised of an anti-apoptotic or pro-apoptotic polypeptide from the BCL-2 family (FIG. 10). The sequences of these polypeptides are readily available on GenBank and in the scientific literature. The Bcl-2 related polypeptide can be a conservatively substituted variant of the naturally-occurring sequence, or a fragment thereof.

A conservatively substituted variant is an amino acid sequence having a conservative amino acid substitution of one or more of the amino acid positions in a naturally-occurring mammalian sequence. Conservative amino acid substitutions refer to the interchangeability of residues having similar side chains. Conservatively substituted amino acids can be grouped according to the chemical properties of their side chains. For example, one grouping of amino acids includes those amino acids which have neutral and hydrophobic side chains (A, V, L, I, P, W, F, and M); another grouping is those amino acids having neutral and polar side chains (G, S, T, Y, C, N, and Q); another grouping is those amino acids having basic side chains (K, R, and H); another grouping is those amino acids having acidic side chains (D and E); another grouping is those amino acids having aliphatic side chains (G, A, V, L, and I); another grouping is those amino acids having aliphatic-hydroxyl side chains (S and T); another grouping is those amino acids having amine-containing side chains (N, Q, K, R, and H); another grouping is those amino acids having aromatic side chains (F, Y, and W); and another grouping is those amino acids having sulfur-containing side chains (C and M). Preferred conservative amino acid substitutions are: R-K; E-D, Y-F, L-M; V-I, and Q-H.

Fragments of BCL-2 related polypeptides useful in the invention should have sufficient length to form a channel in a lipid bilayer. Construction of such fragments and testing them for channel forming activity can be done using well-known deletion-mutagenesis procedures and the procedures described herein.

The channel can also be formed by any subsequently discovered BCL-2 family member that has channel forming activity in vitro and has anti-apoptotic or pro-apoptotic activity.

Preferably, the polypeptide used to form the channel lacks a C-terminal membrane-anchoring tail (TM) to eliminate interference by this hydrophobic anchor with the channel forming activity of other portions of the polypeptide during in vitro studies with lipid bilayers. All known mammalian BCL-2 family members other than BID and BAD contain a TM (FIG. 10). A polypeptide lacking the TM (ΔTM) can be prepared by expression from a cDNA in which the DNA sequences encoding the TM have been removed from a cDNA encoding the full-length BCL-2 family member using standard deletion mutagenesis techniques. cDNA clones encoding full-length BCL-2 family member proteins are either publicly available or readily obtainable using published sequences.

A preferred anti-apoptotic polypeptide for forming the channel is Bcl-2ΔC21 which comprises amino acids 1–218 or 1–221 of human or mouse Bcl-2 shown in FIG. 11 or a conservatively substituted variant thereof. For pro-apoptotic channels, the preferred pro-apoptotic polypeptide is BaxΔC19, which comprises amino acids 1–173 of human or mouse BAX as shown in FIG. 11, or a conservatively substituted variant thereof.

The channel can be formed by adding the polypeptide to the aqueous solution on either or both sides of the bilayer and then mixing the solution. Preferably, the polypeptide is added to only one side of the bilayer which is designated as the cis side. Typically, the concentration of the polypeptide in the aqueous solution is between about 5 and 500 nM, preferably between about 10 and 250 nM, more preferably between about 20 and 125 nM, and even more preferably between about 40 and 60 nM. The aqueous solution is buffered to a pH of between about 4.0 and 7.2. Because low pH promotes insertion into planar bilayers of polypeptides from the BCL-2 family, the aqueous solution is preferably between pH 4.0 and 6.0. The pH of the solution is preferably adjusted to between 6.8 and 7.2 before determining the ion selectivity of the channel.

The polypeptide is preferably incorporated into the planar lipid bilayer at neutral pH by fusing the bilayer with a reconstituted unilamellar proteoliposome comprising the polypeptide. Proteoliposomes can be prepared from purified polypeptides and lipids by standard techniques known in the art, including dialysis, gel filtration and dilution techniques. A membrane fragment vesicle preparation of an intracellular membrane where the BCL-2 family member polypeptide is found in vivo can also be used as a source of proteoliposomes.

Preferably, the dialysis approach is used and involves adding about 7.5 to 15 $\mu$mole of a polypeptide from the BCL-2 family to about 25 to 75 mg lipid in a buffered solution at a pH of about 6.8 to 7.2. This protein-lipid solution is placed in a dialysis bag with a molecular weight cutoff size selected to make the dialysis bag impermeable to lipid and polypeptide but is permeable to any detergent in the polypeptide preparation. Dialysis is performed in a large volume of aqueous solution buffered at about pH 6.8 to 7.2 until unilamellar proteoliposomes form, usually about 10 to 20 hours.

Once prepared, the proteoliposomes are added to one or both sides, preferably the cis side, of a pre-established planar bilayer with mixing until fusion occurs. As an alternative or in addition to mixing, fusion can be initiated by electrofusion, in which a high electric field pulse is applied to the bilayer chamber. Preferably, about 5–20 $\mu$l of proteoliposomes, comprising about $2.0 \times 10^{-4}$ to $10 \times 10^{-4}$ nmoles polypeptide incorporated in Azolectin vesicles, are added to the cis side of a planar lipid bilayer.

Formation of a channel by the polypeptide is verified by applying a voltage and assaying for a current above noise and leak values. Once an initial channel current is identified, soluble polypeptide or proteoliposomes unincorporated in the bilayer can then be removed from the chamber by exchanging the chamber contents with fresh buffer.

Prior to or following addition of the channel-forming polypeptide, the concentration of ions in one or both compartments of the bilayer chamber is adjusted to establish an ion concentration gradient between the compartments so that ion selectivity of the channel can be determined. A concentration gradient means that the concentration of cations and the concentration of ions on one side of the bilayer are both higher than on the other side of the bilayer. The concentrations of cations and anions on a particular side of the bilayer need not be equivalent to each other but it is preferable that they are approximately equal. If the concentration gradient is set up before addition of the polypeptide, the ion selectivity of the initial currents can be identified.

The ion concentration gradient is generally between 2- and 100-fold cis:trans and preferably is between about 3-fold and 10-fold cis:trans. Alternatively, similar gradients can be set up trans:cis. Examples of ion concentration gradients typically used are 150:15 $\mu$M, 450:150 $\mu$M, and 1.0:0.5 M.

To determine if a compound of interest has cell death promoting or cell death antagonizing activity, the compound is added to either side of a planar bilayer comprising a channel comprised of an anti-apoptotic or pro-apoptotic polypeptide of the BCL-2 family. The ion selectivity of the channel is determined in the presence of an ion concentration gradient which can be established before or after addition of the compound. If the ion selectivity of an anti-apoptotic channel changes from cation-selective to anion-selective in the presence of the compound, the compound is a cell death agonist. Conversely, if the compound changes the ion selectivity of a pro-apoptotic channel from anion-selective to cation-selective, the compound is a cell death antagonist. Preferably, the compound is tested at several different concentrations to determine the lowest amount that is effective in changing ion selectivity.

The compound's activity can be further characterized by determining whether it affects the conductance pattern and rectification of the channel. These channel properties are assessed by measuring the current at different negative and positive voltages when equivalent ion concentrations are present on both sides of the planar bilayer. Based on the distinct characteristics of Bcl-2 and Bax channels and the behavior of the Bcl-2 channel in the absence and presence of an 11mer peptide with death agonist activity, it is believed that a compound with death agonist activity will impart a pro-apoptotic conductance pattern and rectification to an anti-apoptotic channel.

In a preferred embodiment, the compound is also tested for its ability to insert into membranes to form a channel and for the effect of pH on any such channel forming activity. This can be accomplished by the incubating the compound with lipid vesicles in solutions at different pH values between 3.5 and 7.0 as described below. If the compound has both cation selectivity and its channel forming activity is affected by pH in a manner similar to that of Bax, the compound is more likely to be pro-apoptotic under conditions that activate native apoptosis agonists. Conversely, if the compound has both anion selectivity and its channel forming activity at acidic and neutral pH is similar to that of Bcl-2, the compound is more likely to be anti-apoptotic under conditions that activate native apoptosis antagonists.

In one embodiment of the invention, the lipid bilayer comprises a unilamellar proteoliposome loaded with a mixture of cations and anions in known amounts and the effect of a compound on the relative rates of cation and anion efflux from the proteoliposome is determined. The unilamellar proteoliposome can be prepared as described above or by any other technique known in the art. Preferably the mixture of cations and ions comprises equal amounts of $K^+$ and $Cl^-$. Cation or anion efflux can be measured with cation- or anion-specific electrodes or alternatively by a dye which reacts with the cation or anion in a concentration dependent manner.

The relative rates of cation and anion efflux rates from the vesicles is compared in the absence and presence of a compound of interest. If the compound induces a faster rate of anion efflux from a proteoliposome comprising an anti-apoptotic channel, it has death agonist activity. Conversely, if the compound induces a faster rate of cation efflux from a proteoliposome comprising a pro-apoptotic channel, it has death antagonist activity.

The invention also provides a method for identifying apoptosis modulating compounds based on their ability to both form a cation- or anion-selective channel in a lipid bilayer and by the effect of pH on their channel forming activity in lipid vesicles. The lipid bilayer lacks preformed channels and can be a planar bilayer or a liposome loaded with cations and anions. A compound of interest is added to the bilayer and ion selectivity is determined as described in the planar bilayer and proteoliposome experiments described above. Preferably, the method comprises assaying for formation of $K^+$ and/or $Cl^-$-selective channels.

The effect of pH on channel forming activity is quantified by incubating the test compound with lipid vesicles in separate solutions at pH values between 3.5 and 7.0 (e.g., pH 4.0, 5.0, 6.0, 7.0 and others as required). The lipid vesicles comprise a lipid bilayer surrounding an aqueous interior which contains a channel indicator. The channel indicator is any substance that is detectable upon release from the vesicle. For example, the indicator can be a detectable ion or a substrate that forms a detectable reaction product upon contact with an enzyme located outside the vesicle, or a fluorescent compound such as carboxyfluorescein or fluorescein-dextran that increases intensity when its release from the vesicle removes concentration dependent quenching.

The test compound is incubated with vesicles at the desired pH values for the same length of time. At the end of the incubation period, the amount of channel indicator released at each pH is then determined. The channel indicator is detected by an electrode or spectrophotometer appropriate for the type of indicator used. If no channel indicator is released, then the compound does not form channels. If the ratio of release at pH 3.5 to that at pH 4.0 ($R_{3.5/4.0}$) is less than 1 and the ratio of release at pH 4.0 to that at pH 5.0 ($R_{4.0/5.0}$) is between 1 and 2, the compound is inserting under pH conditions that favor channel formation by anti-apoptotic compounds. An $R_{3.5/4.0}$ of approximately 1 accompanied by an ($R_{4.0/5.0}$) of greater than 7 indicates the compound is inserting under pH conditions that favor channel formation by anti-apoptotic compounds. This information allows the prediction of channel forming characteristics of compounds having ion selectivities appropriate to pro- or anti-apoptotic action. With compounds that vary in structure it may be useful to assess the pH dependence of channel formation using a broader pH range, for example between pH 3.5 and 8.0.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates that Bax and Bcl-2 induce the release of ions from synthetic lipid vesicles.

The Bax and Bcl-2 polypeptides used in the ion channel studies reported herein were recombinant murine Bcl-2 and Bax polypeptides lacking the C-terminal signal-anchor membrane targeting sequence (Bcl-2ΔC21, amino acids 1–218 of SEQ ID NO:9 and BaxΔC19, amino acids 1–173 of SEQ ID NO:6). These deletion derivatives, also referred to herein as BaxΔTM and Bcl-2ΔTM, were used to avoid any interference of the C-terminal signal-anchor membrane targeting sequence with the capacity of internal α helices to mediate insertion into artificial lipid bilayers.

To produce Bcl-2ΔC21 and BaxΔC19A, cDNAs encoding amino acids 1–218 of murine Bcl-2 (SEQ ID NO:9) and amino acids 1–173 of murine Bax (SEQ ID NO:6) were cloned into pGEX-KG. The resulting recombinant vectors were transformed into XL-1 cells and expression of GST-Bcl-2ΔC21 and GST-BaxΔC19A fusion proteins was induced by adding 0.1 mM IPTG. The bacterial pellets were resuspended in lysis buffer (0.5 mM EDTA, 1 mM DTT, 1% Triton X-100, 0.1 mg/ml PMSF, 2 ug/ml aprotinin, 2 ug/ml leupeptine and 1 ug/ml pepstatin A in PBS) and sonicated. After centrifugation at 20,000×g for 20 minutes, the supernatant was applied to glutathione-agarose beads (Sigma). The beads were washed with buffer and treated with 10 units of thrombin/original liter. Cleaved BaxΔC19 and Bcl-2ΔC21 were eluted from beads and the cleavage reaction was terminated by adding 80 ug of Na-p-tosyl-L-lysine choloromethyl ketone (TLCK). The cleaved eluent was dialyzed against buffer (20 mM Tris pH 8.5, 5 mM EDTA, 1 mM DTT, 0.1% Triton X-100). To remove the GST protein and incompletely cleaved fusion proteins, the dialyzed preparation was further purified on a monoQ column and the proteins were eluted with a NaCl gradient. The examples described below utilized 3 independent protein preparations of Bax and Bcl-2.

EXAMPLE 2

This example illustrates that Bax and Bcl-2 form channels in planar lipid bilayers at low pH.

Unilamellar vesicles composed of 40% 1,2 dioleoyl phosphatidyl glycerol and 60% 1,2 dioleoyl phosphatidyl choline (Avanti Polar Lipids) were prepared in 100 mM KCl, 2 mM $CaNO_3$ and 10 mM dimethylglutarate, pH 5.0 as previously described (Peterson et al., *J. Membr. Biol.* 99:197–204, 1987). The resulting liposomes were diluted 200-fold to a concentration of 0.05 mg/ml in 100 mM $KNO_3$, 2 mM $CaNO_3$ and 10 mM dimethylglutarate which was titrated to pH 3.5, 4.0, 4.5, 5.0, 5.5 or 6.0 with NaOH or with acetic acid. BaxΔC19 and Bcl-2ΔC21 were added at a concentration of 500 ng/ml and $Cl^-$ efflux was measured with a $Cl^-$ combination ion selective electrode (Accumet). Triton X-100 (0.1%) was added to release the total encapsulated $Cl^-$ at the times indicated by the arrows in FIG. 1. The total amount of $Cl^-$ released was quantitated by a calibration curve produced by successive additions of 25 μM KCl.

Figure 1B:
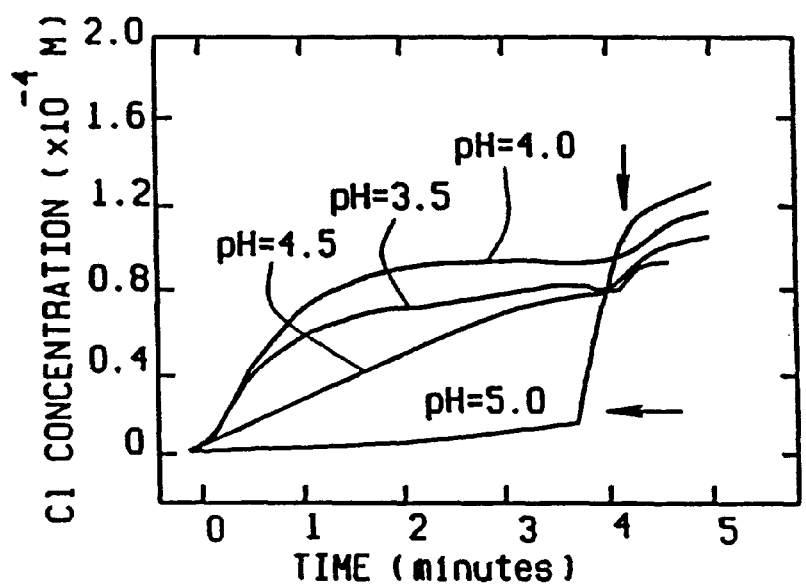
Figure 1C:
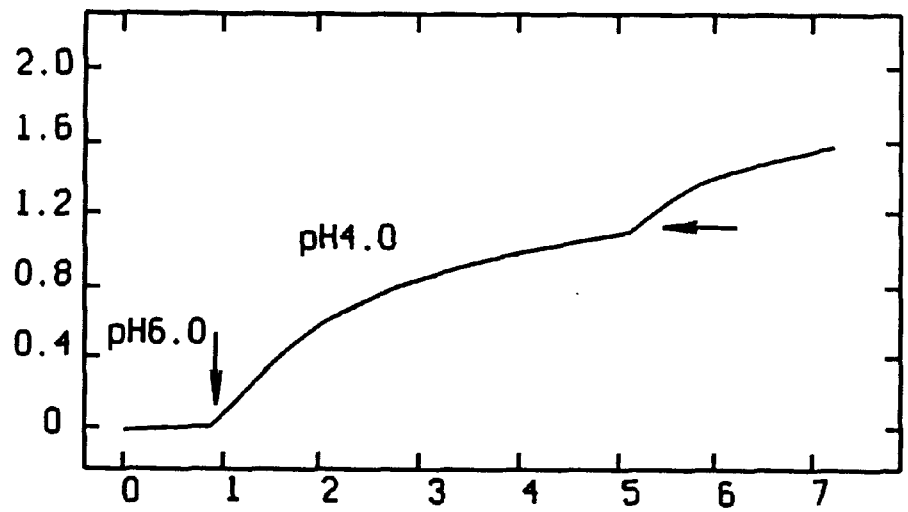
Figure 1D:
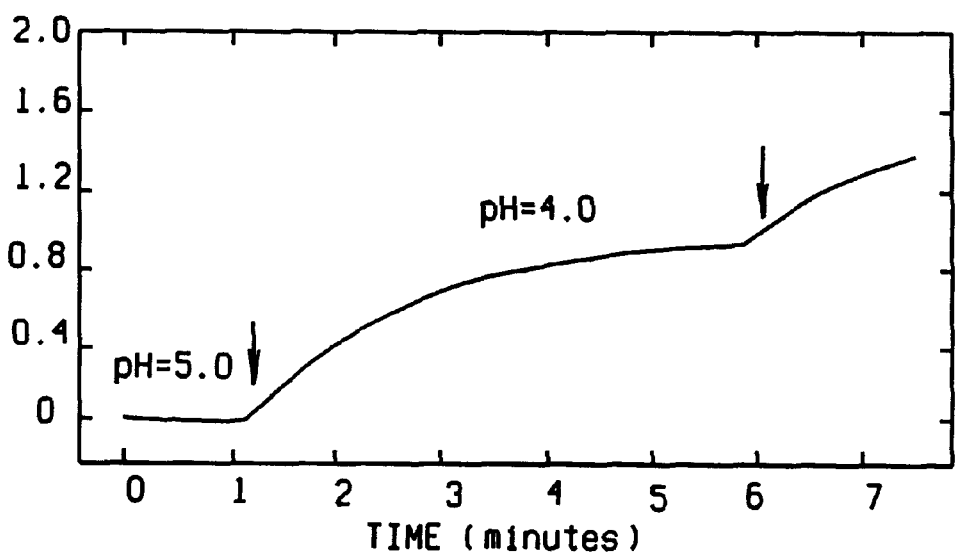

As shown in FIGS. 1A–D, Bax and Bcl-2 mediated release of $Cl^-$ from KCl loaded lipid vesicles is dependent on pH (FIGS. 1B–E). The maximum release of $Cl^-$ by Bax occurs at pH 4.0–4.5, decreasing to 50% at pH 3.5 or 5.0 and to less than 10% at a pH of 5.5 (FIG. 1A). When Bax added to vesicles at pH 6.0 was subsequently shifted to pH 4.0 a rapid release of $Cl^-$ resulted indicating the reversibility of the pH influence (FIG. 1C). Bcl-2 displays a more narrow pH dependence of $Cl^-$ release with complete inactivation occurring by pH 5.0 (FIG. 1B). Shifting from pH 5.0 to 4.0 activated the release of $Cl^-$ by Bcl-2 (FIG. 1D). Thus, both purified Bax and Bcl-2 proteins are capable of pH dependent macroscopic ion release requiring activity of the bulk population of Bcl-2 and Bax proteins.

EXAMPLE 3

This example illustrates the formation of Bax channels in planar lipid bilayers at low pH.

Planar lipid bilayers were prepared from soybean lipids by chloroform extraction of Azolectin Type II (10–20% choline, 80–90% negatively charged lipids) (Sigma). The chloroform was removed with a stream of nitrogen and the lipids stored under $N_2$ until dissolved in decane at 30 mg/ml. This preparation was then stored under nitrogen. The 0.25 mm orifice of a polystyrene cuvette (Warner Instruments) was pretreated with 2 μl of the decane lipid solution and the solvent allowed to evaporate. The cuvette was then placed into a bilayer chamber and connected to Bilayer Clamp BC525-a (Warner Instruments) by Ag/AgCl electrodes via agar salt bridges. Data were collected using an Axoscope (Axon Instruments Software), archived on video tape using a Neurocorder DR-484 (Neuro Data Instruments), and analyzed using Origin (Microcal) and pClamp6 (Axon Instruments Software). Slope conductance was calculated by the method of least squares and the variance is given. Ion selectivities were calculated using the reversal potential and the Goldman equation. The reversal potential means the zero-current potential of a bilayer membrane. The reversal potential is zero with no ion gradient and the magnitude of the potential in the presence of an ion gradient reflects the cation versus anion selectivity of the bilayer.

Bilayers were formed by spreading with a polished glass rod and allowed to thin to a capacitance of 0.4 $\mu F/cm^2$ at which point the noise was typically 0.2 pA and the leak conductance was 20 pS. The salt concentrations were initially 450 mM KCl in the cis chamber (1.0 ml) and 150 mM KCl in the trans chamber (0.5 ml) to permit identification of spontaneous initial currents. Outward (positive) currents were defined as $K^+$ moving cis-to trans. All solutions were buffered to pH 4.0 with 10 mM K-acetate. BaxΔTM or Bcl-2ΔTM (approx. 1 μg) was added to the cis chamber with mixing. After initial currents were identified the soluble protein was usually removed by exchanging the cis chamber contents with aliquots of buffer.

Figure 2A:
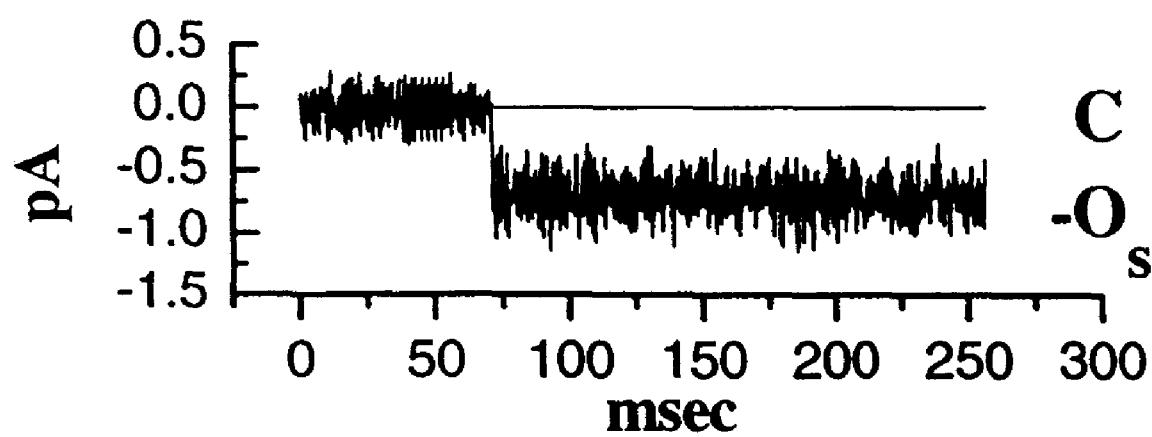
FIGS. 2A–2C illustrates the low pH formation of Bax channels in planar lipid bilayers as characterized by the currents appearing after addition of BaxΔTM to the cis chamber of an established planar lipid bilayer in a 450/150 mM cis to trans KCl gradient at pH 4.0, showing (FIG. 2A) a tracing of an initial, inward Cl⁻ current that appeared spontaneously at 0 volts ($O_S$), (FIG. 2B) tracings of the currents that occurred at +40 mV (upper tracing) or −40 mV (lower tracing) after removal of soluble BaxΔTM from the cis chamber showing the transition from the $O_S$ to a large open pore with * denoting a direct C-$O_S$ to $O_2$ transition, and (FIGS. 2C and 2D) current-voltage (I/V) plots for the mature pore at pH 4.0 (FIG. 2C) and following a shift to pH 7.0 in the presence of the 450/150 mM KCl gradient (open circle) or in symmetric 150 mM KCl (filled square) (FIG. 2D)

Four minutes after BaxΔTM was added to the cis chamber of an established planar lipid bilayer in a 450/150 mM (cis to trans) KCl gradient at pH 4.0, an initial, inward current appeared spontaneously ($O_S$), reflecting $Cl^-$ moving down the KCl gradient (FIG. 2A). The initial current of the Bax channel had consistent characteristics in multiple experiments: it was always inward, usually appeared within 10 minutes following BAXΔTM addition, and had a conductance of 22 (s.d. 5, n=5) pS.

Figure 2B:
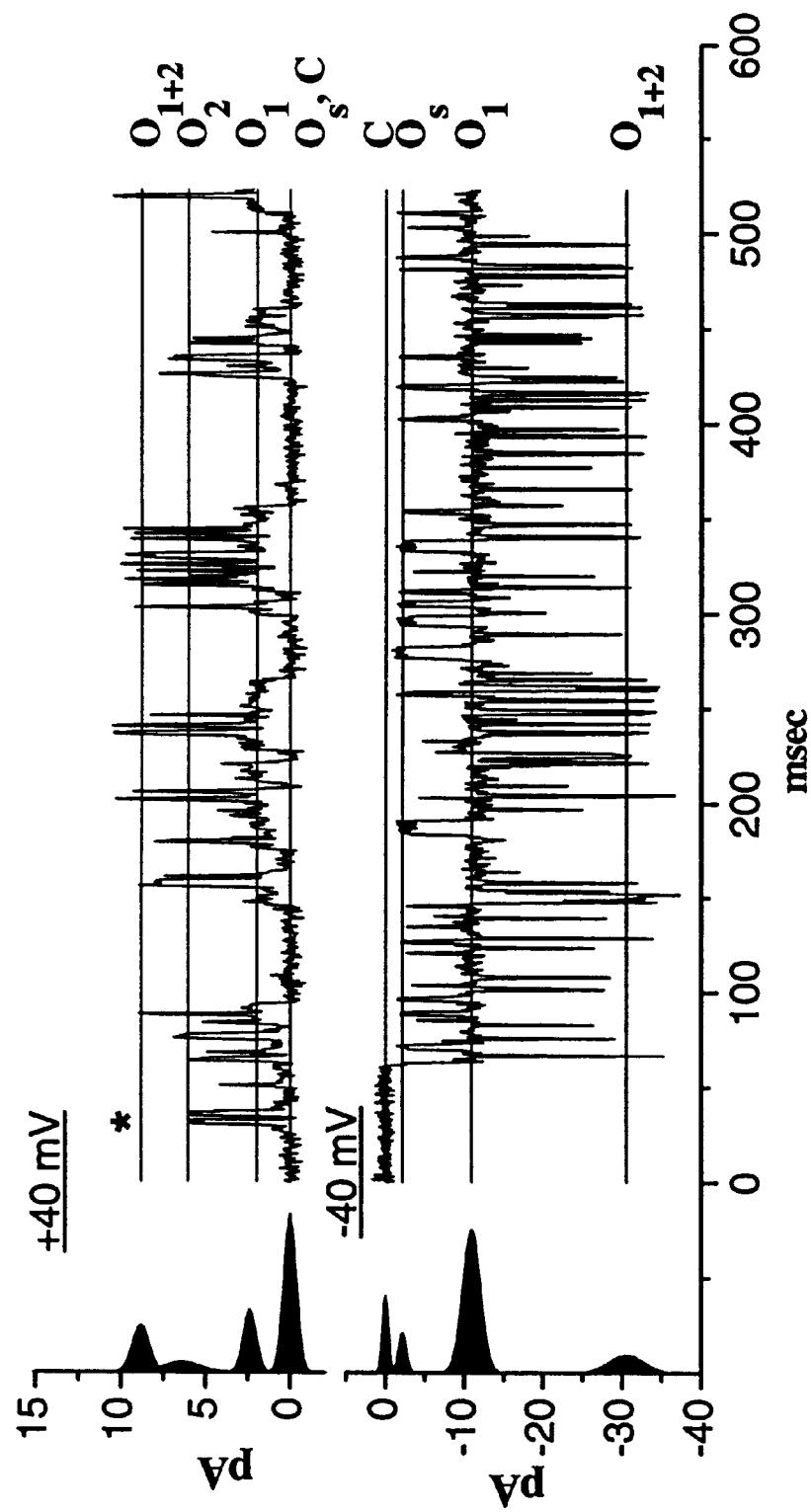

As shown in FIG. 2B, a characteristic pattern of Bax currents occurred during a transition from $O_S$ to a large open pore. At +40 mV four current levels were noted during a typical Bax channel transition which took ~5 mins.: 0 pA (C and $O_S$), 2.36 pA ($O_1$), 6.4 pA ($O_2$) and 8.81 pA ($O_{1+2}$) (FIG. 2B, upper panel). The largest current appears to be the sum of the two smaller levels ($O_1$ and $O_2$). The closed (C) and $O_S$ levels are indistinguishable at +40 mV as it is close to the chloride reversal potential ($E_R$=29 mV). Direct transitions between these levels, which occur in both directions, suggest a random mechanism for movement between the open states (FIG. 2B). At −40 mV there were also four levels: 0 pA (C), −2.14 pA ($O_S$), −10.9 pA ($O_1$), −30.5 pA ($O_{1+2}$), but no observable $O_s$ to $O_2$ transition (FIG. 2B, lower panel). Hyperpolarization to −40 mV increased the channel activity, demonstrating voltage dependent behavior of the channel. Computing the $E_R$ for each of these current levels gives a substantial $Cl^-$ selectivity that averages $P_K/P_{Cl}$=0.10. The final and apparently stable BAX channel at pH 4.0 was $Cl^-$ selective, with a slope conductance of 0.731±0.01 nS and was characteristically open.

Figure 2C:
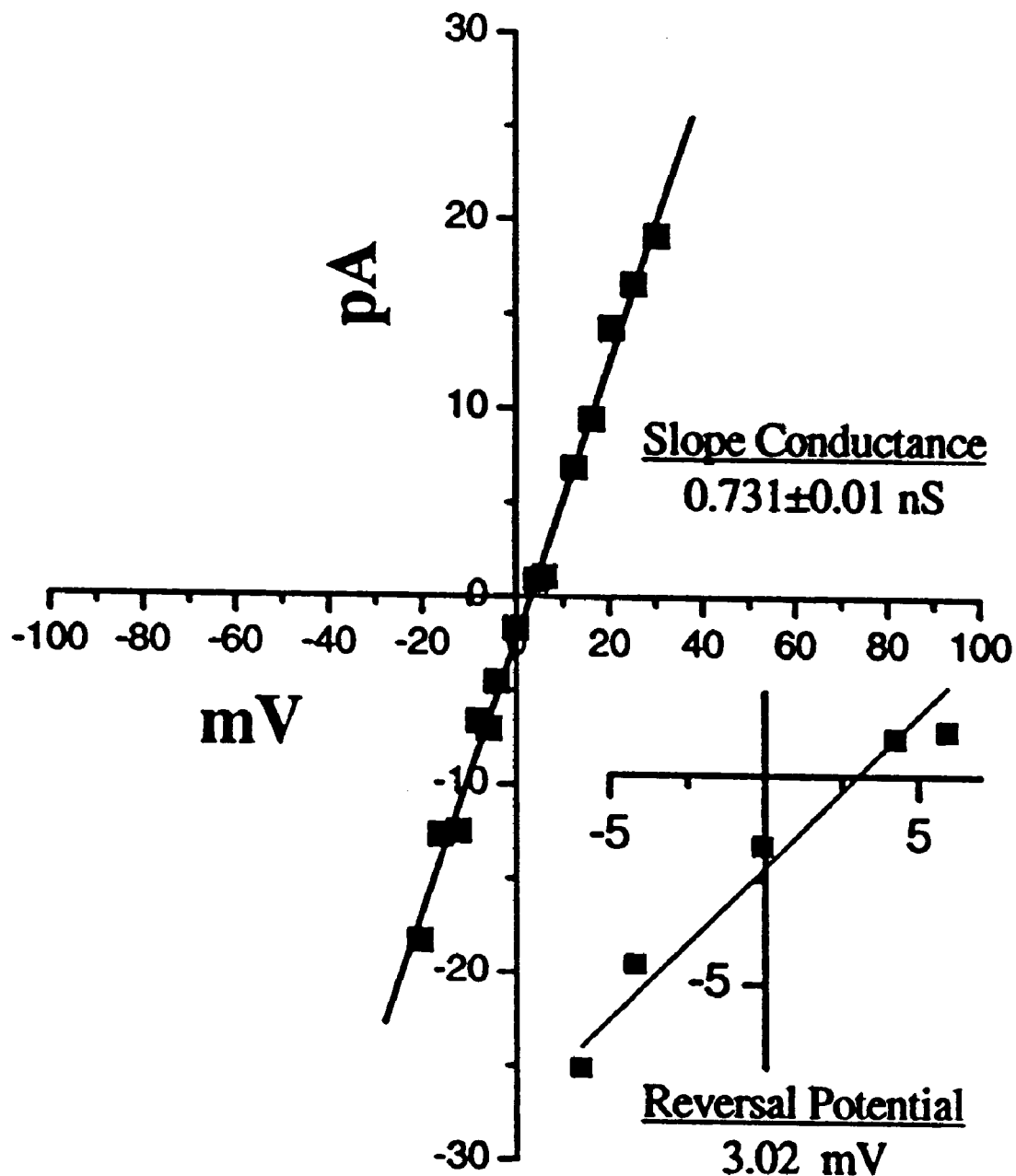
Figure 2D:
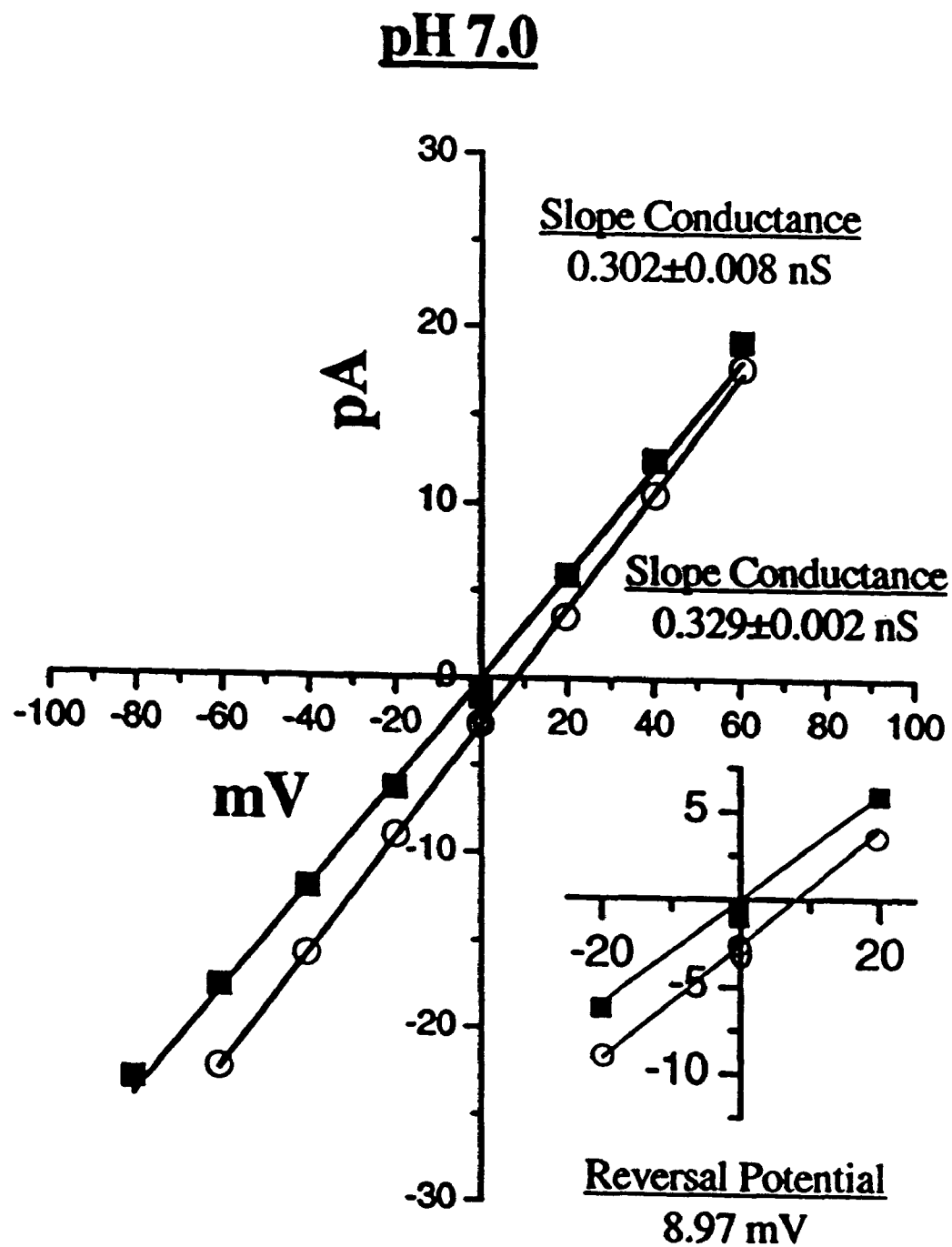

This progression of Bax channels proceeded after the removal of protein from the cis chamber. Increasing the pH to 7.0 altered the conductance of the Bax channel to 0.329±0.002 nS in a 450/150 mM KCl gradient or to 0.302±0.008 nS when both chambers were 150 mM KCl (FIGS. 2C, 2D). The Bax channel was observed in this activity state at pH 7.0 for prolonged periods. At pH 7.0, the current of the Bax channel was linear with voltage and retained a mild selectivity for $Cl^-$ ($P_K/P_{Cl}$=0.5).

EXAMPLE 4

This example illustrates the formation of Bax channels in planar lipid bilayers at pH 7.0 following fusion of the planar bilayer with unilamellar proteoliposomes reconstituted with BaxΔTM.

Proteoliposomes for fusion with a planar lipid bilayer were prepared as follows. Purified protein (0.25 μg) was added to 50 mg lipid (Azolectin) in 20 μl of KCl buffer (150 mM KCl, 10 mM HEPES, pH 7.0). This mixture was placed into a dialysis bag with a molecular weight cutoff of 12 KDa. After 16 hours dialysis in 3000 volumes of 150 mM KCl (10 mM HEPES, pH 7.0) the proteoliposome suspension was removed and placed on ice for immediate use. The bilayer was set up with a 450:150 cis to trans KCl gradient to identify the ion selectivity of the initial currents. Fusion was initiated by adding 5–20 μl of lipid vesicles (only 5–20 ng of protein) to the cis bilayer chamber with mixing. Non-fused proteoliposomes were removed from the compartments and solutions exchanged as described above.

Figure 3A:
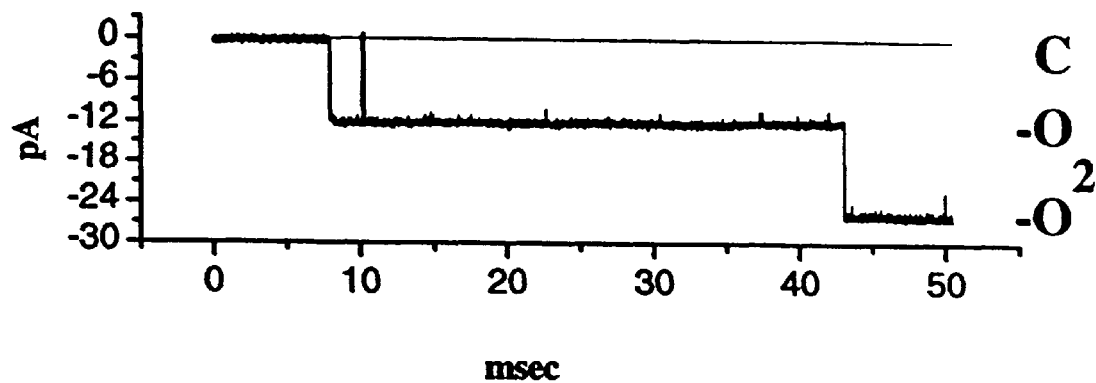
FIGS. 3A–3B illustrates the incorporation of Bax into planar lipid bilayer membranes following addition of BaxΔTM-containing unilamellar proteoliposomes to the cis chamber of an established lipid bilayer, showing (FIG. 3A) a tracing of an initial inward Cl⁻-selective current in the presence of a 450/150 mM KCl gradient, (FIG. 3B) tracings of the current of a single Bax channel in symmetrical 150 mM KCl at different voltages, (FIG. 3C) an I/V plot of the Bax channel, and (FIG. 3D) longer tracings of the current which demonstrate rectification at 70 mV (upper tracing) and closures at −70 mv (lower tracing)

BaxΔTM was incorporated into lipid vesicles using standard techniques. The resulting Bax proteoliposomes were added to the cis chamber of an established lipid bilayer with a 450/150 mM KCl gradient at pH 7.0 to permit identification of initial currents. The inward ($P_K$<$P_{Cl}$) current observed was characteristically open and large. Transitions between one and two channels open (0→$0^2$, FIG. 3A) that were identical in amplitude suggested that 0 represented the single channel conductance (FIG. 3A). A mild $Cl^-$ selectivity ($P_K/P_{Cl}$=0.32) was calculated from the reversal potential.

Figure 3B:
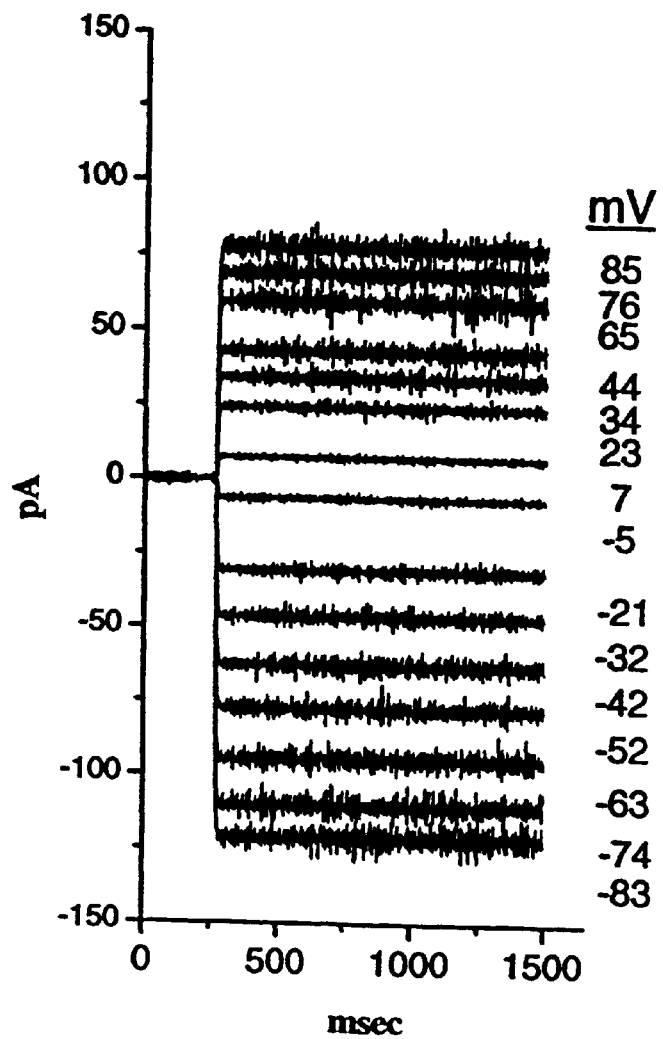
Figure 3C:
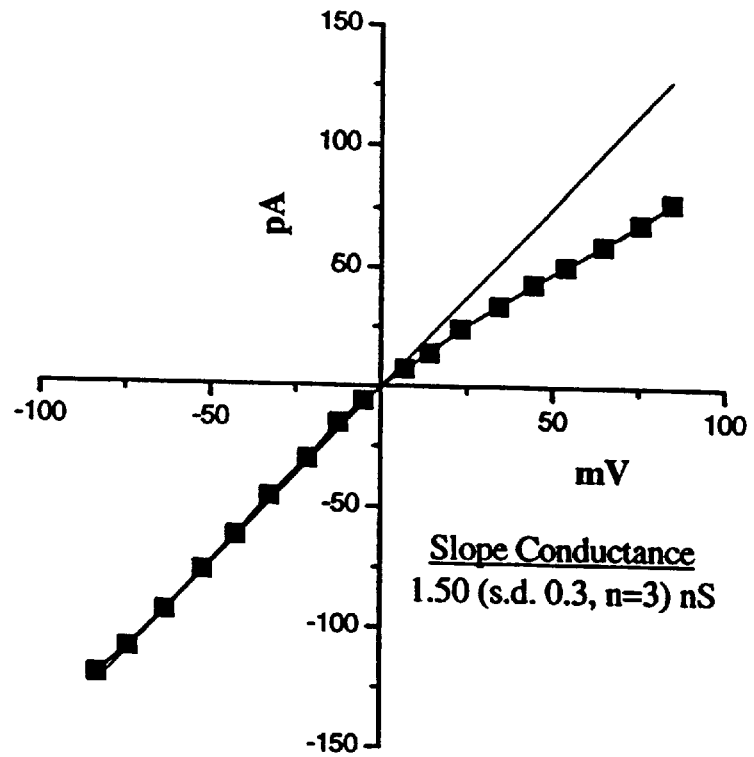
Figure 3D:
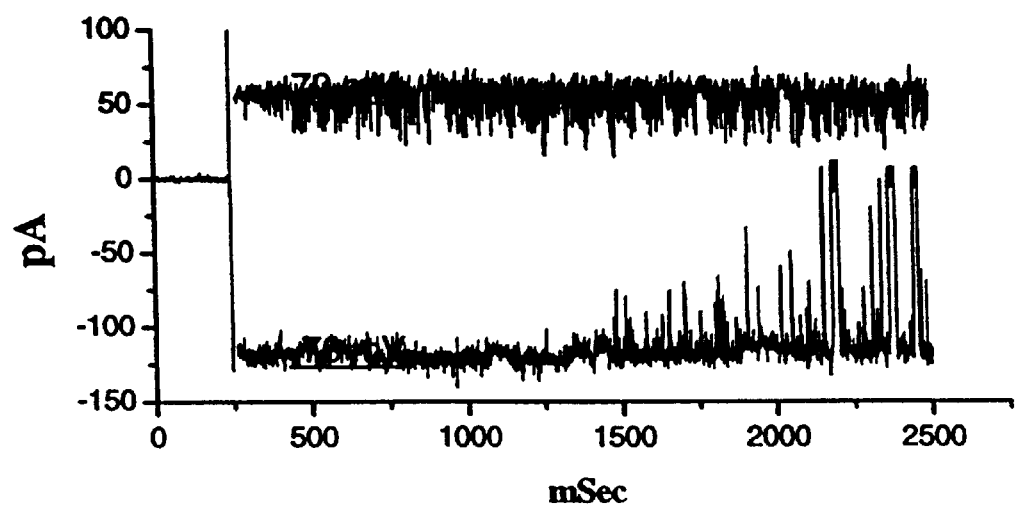

The concentration of KCl was adjusted to 150 mM KCl in both cis and trans compartments and voltage dependence of the current was determined when one channel was present (FIGS. 3B and 3C). Mild outward rectification in the symmetrical KCl solution was observed. At negative voltages the channel conductance averaged 1.5 (sd 0.3, n=3) nS (FIG. 3C), while at positive voltages (+70 mV) the rapid flickering was consistent with channel block as a mechanism for the rectification seen in FIG. 3B. At −70 mV there was no flickering but periodic closing of 20–30 msec duration was observed (FIG. 3C), a pattern similar to that reported for porin type channels (Benz, *Biochim. Biophys. Acta* 1197:167–196, 1994).

EXAMPLE 5

This example illustrates the formation of Bcl-2 channels in planar lipid bilayers at low pH.

Figure 4A:
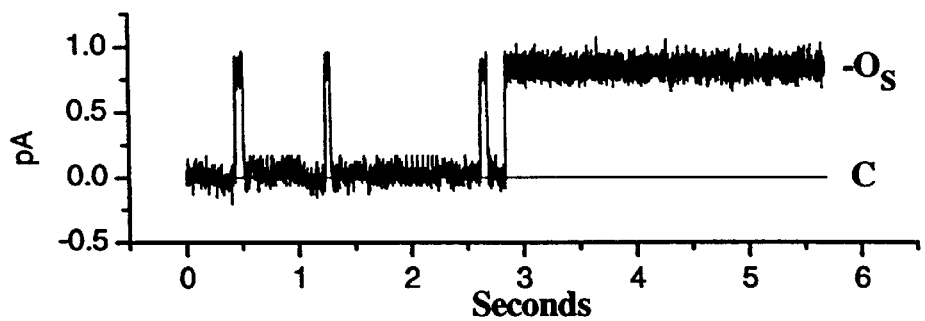
FIGS. 4A–4E illustrates the low pH formation of Bcl-2 channels in planar lipid bilayers as characterized by the currents appearing after addition of Bcl-2ΔTM to the cis chamber of an established planar lipid bilayer in a 450/150 mM cis to trans KCl gradient at pH 4.0, showing (FIG. 4A) a tracing of an initial, outward K⁺ current that appeared spontaneously at 0 volts ($O_S$), (FIG. 4B) channel transitions between the open ($O_S$) and closed (c) states at 0 volts for three duplicate experiments, (FIG. 4C) a histogram of the distribution of current amplitudes for the channel over 120 seconds, (FIG. 4D) an I/V plot of the Bcl-2 channel from (B), and (FIG. 4E) an I/V plot of the activity of the large pore that formed over time at pH 4.0 (closed square) and following a shift to pH 7.0 (open square) or in symmetric 150 mM KCl (filled square)

Bcl-2ΔTM was added to the cis chamber of an established bilayer in a 450/150 mM KCl gradient at pH 4.0. An initial outward ($P_K/P_{Cl}$=3.9) current ($O_S$) consistently appeared within 5 minutes in multiple experiments (FIG. 4A). The magnitude of the current was 0.85±0.06 pA which flickered open and shut in the first few seconds and subsequently remained open. Under these conditions, the Bcl-2 channel had a conductance of 80.3±0.06 pS (FIG. 4D).

Figure 4B:
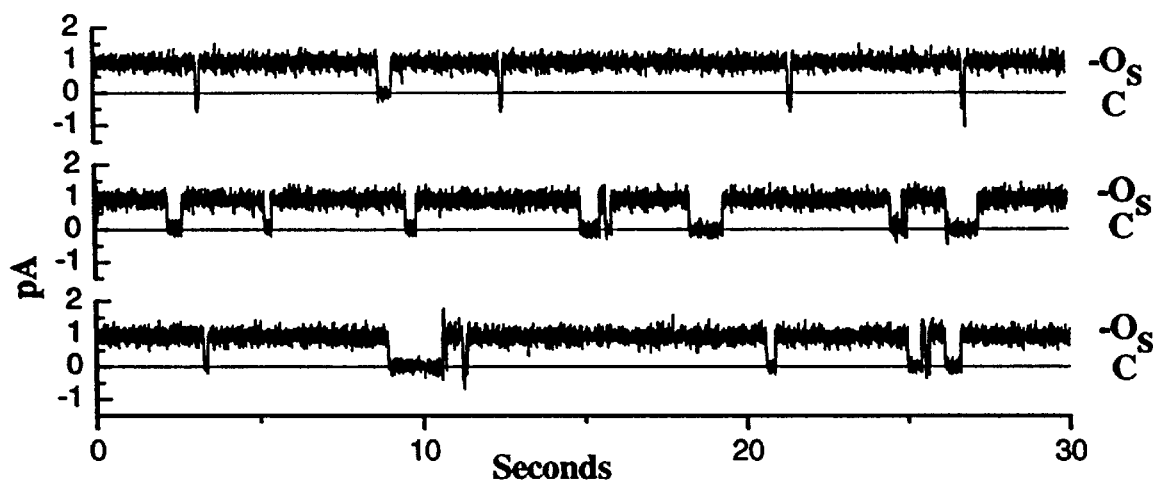
Figure 4C:
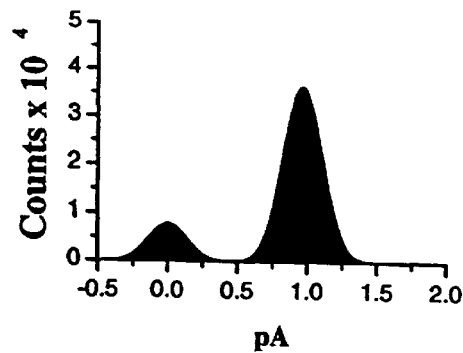
Figure 4D:
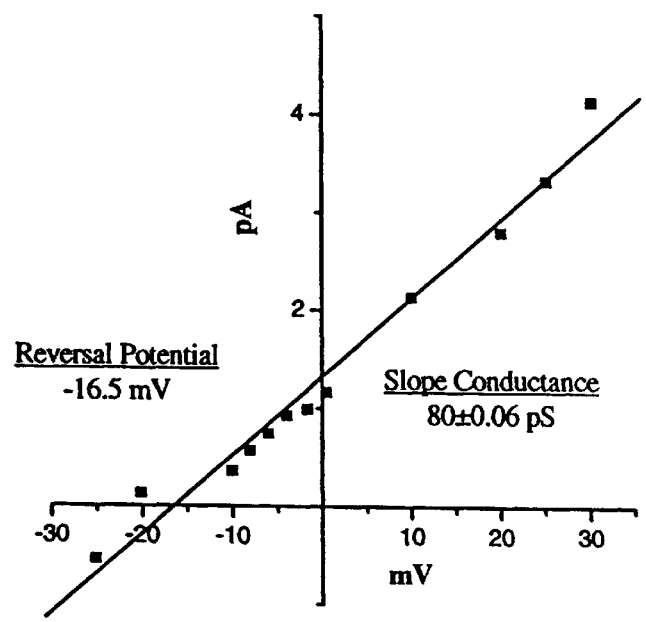
Figure 4E:
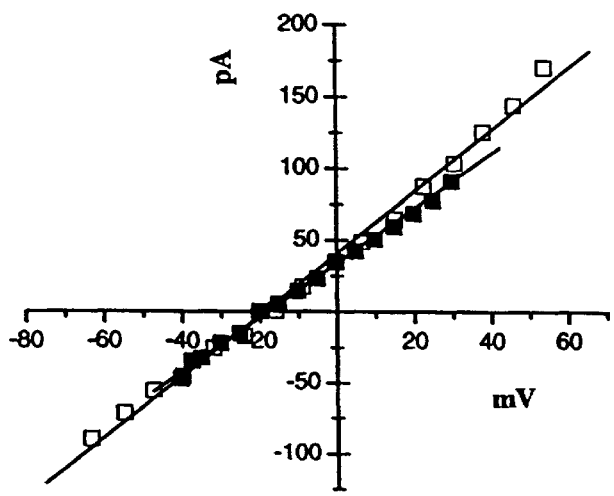

Subsequently, the Bcl-2 channel remained open for long periods (5–10 seconds) with brief closures (FIGS. 4B, 4C). This initial state was present for only 2–5 minutes under these conditions and then the Bcl-2 channel progressed to a stable open pore at pH 4.0 with a 1.90±0.06 nS conductance (FIG. 4E). After the pH was shifted to 7.0, the Bcl-2 channel remained a large pore with a 2.14±0.04 nS conductance and K$^+$ selectivity of P$_K$/P$_{Cl}$=6.5 (FIG. 4E).

EXAMPLE 6

This example illustrates the formation of Bcl-2 channels in planar lipid bilayers at pH 7.0 following fusion of the planar bilayer with unilamellar proteoliposomes reconstituted with Bcl-2ΔTM.

Figure 5A:
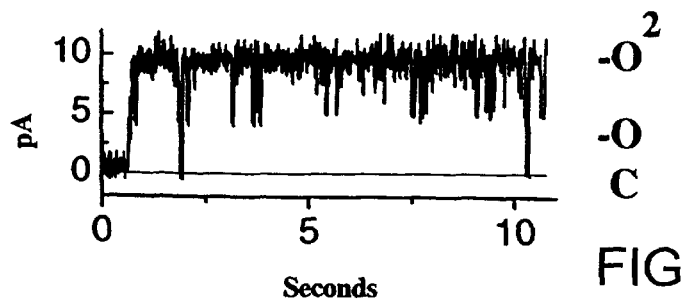
FIGS. 5A–5D illustrates the incorporation of Bcl-2 into planar lipid bilayer membranes following addition of Bcl-2ΔTM-containing unilamellar proteoliposomes to the cis chamber of an established lipid bilayer, showing (FIG. 5A) a tracing of the initial K⁺ current of two Bcl-2 channels that simultaneously appeared in the presence of a 450/150 mM KCl gradient, (FIG. 5B) tracings of the channel current of an established single Bcl-2 channel (upper tracing) resulting from application of a series of voltage steps (lower tracing) to the channel in a 450/150 mM KCl gradient, (FIG. 5C) tracings of a single Bcl-2 channel in symmetrical 150 mM KCl at different voltages, and (FIG. 5D) an I/V plot of the Bcl-2 channel.
Figure 5B:
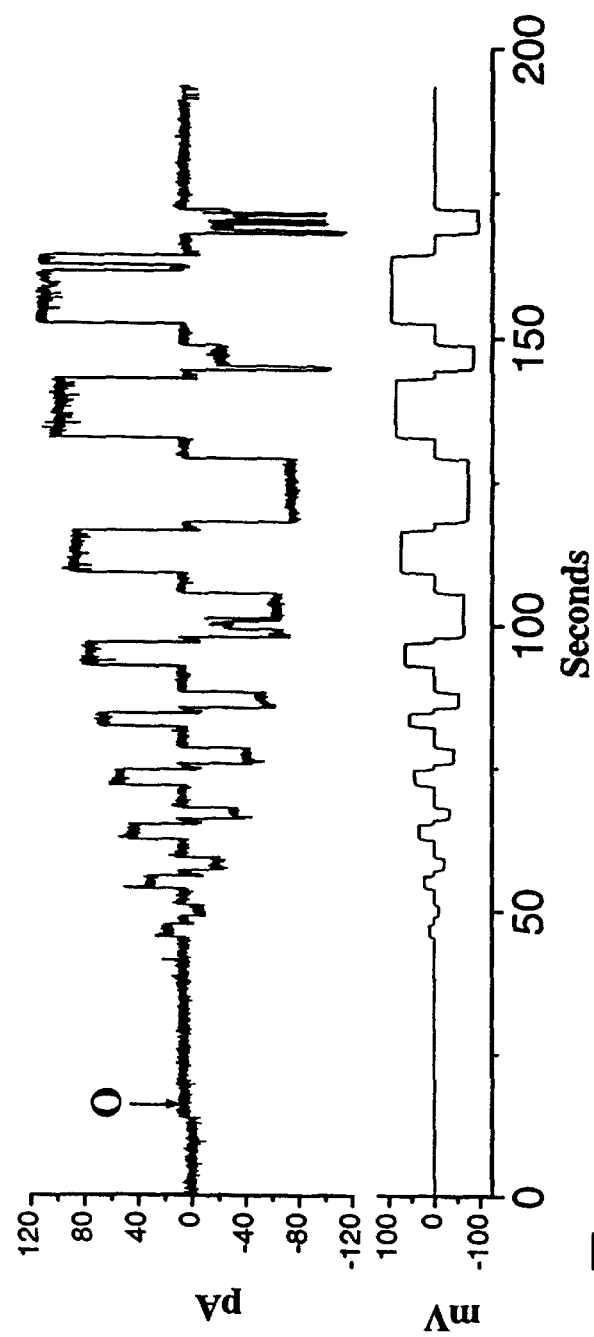

Bcl-2ΔTM proteoliposomes were prepared as described in Example 4 and added to the cis chamber of an established bilayer with a 450/150 mM KCl gradient. In multiple experiments fusion of Bcl-2 proteoliposomes to the bilayer always resulted in an outward (K$^+$) current (FIG. 5A). The closures in FIG. 5A indicate a single channel current of 5 pA (O), although multiple channels could open simultaneously (O$^2$). When a series of voltage steps were applied to a single channel established in the bilayer, channel closures were observed at voltages greater than ±50 mV (FIG. 5B). These closures became more complete as the voltage increased.

Figure 5C:
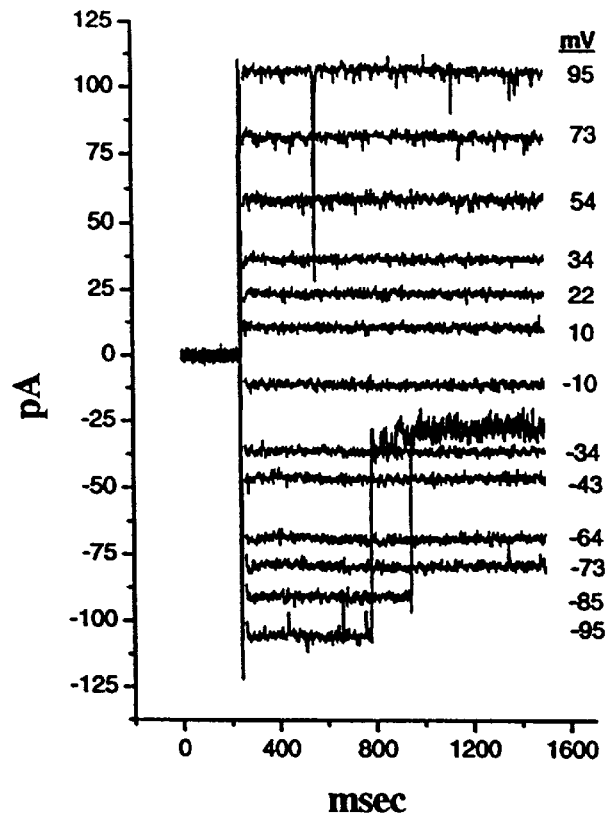
Figure 5D:
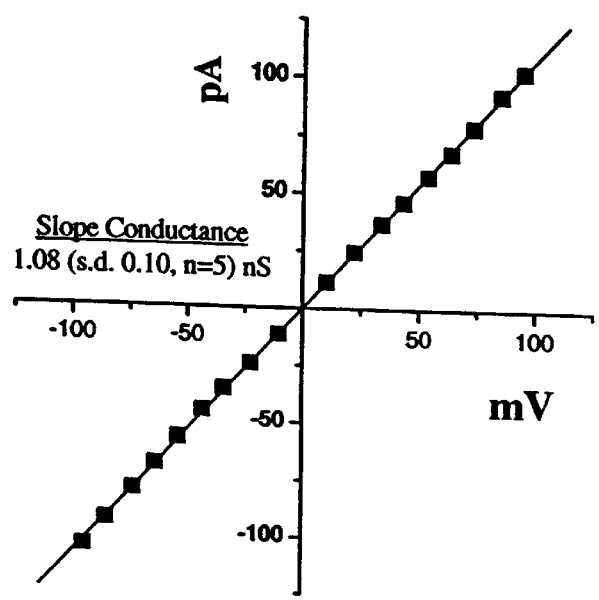

The voltage dependence of the open channel current in symmetrical 150 mM KCl was linear with a slope conductance of 1.08 (s.d. 0.10, n=5) nS (FIGS. 5C and 5D). However, with hyperpolarization to more than −70 mV, a channel closure occurs (FIG. 5C). The reversal potential in KCl gradients indicated a mild K$^+$ selectivity (P$_K$/P$_{Cl}$=2.4). The small channels and time dependent changes noted when Bcl-2ΔTM was inserted into planar lipid bilayers at low pH were not observed when reconstituted proteoliposomes containing Bcl-2ΔTM were fused to planar lipid bilayers at pH 7.0.

EXAMPLE 7

This example illustrates models of the three-dimensional structure of the α-5 and α-6 helices of Bax and Bcl-2.

Figure 6:
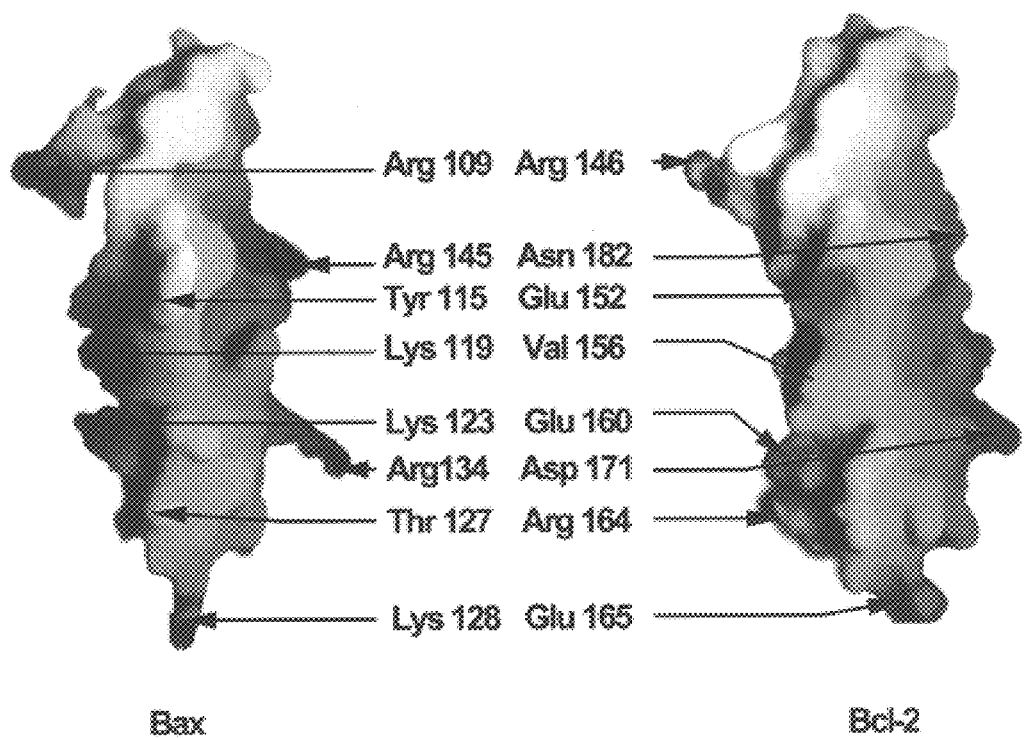

The models were generated using INSIGHTII (Biosym, San Diego) from the crystallographic model of Bcl-x$_L$ (PDB entry 1MAZ). Views of the positively and negatively charged surfaces of the α-5 and α-6 helices of Bax and Bcl-2, respectively, were calculated and displayed as shown in FIG. 6 using GRASP (Nicholls et al., *Protein Struct. Funct. Genet.* 11:281–296, 1991). The surfaces are colored deep blue (15k$_B$T) in the most positively charged regions and deep red (−15k$_B$T) in the most negative, with linear interpolation for values in-between.

The experiments described in Examples 1–6 demonstrate that Bax and Bcl2 have distinct channel forming properties. The inventors herein found that both Bax and Bcl-2 initiate rapid release of ions from liposomes when added at low pH. However, Bax demonstrated a broader pH optimum, retaining activity as high as pH 5.5. It is believed this could be due to the higher α5-helix pI of 10.64 for Bax versus 4.55 for Bcl-2 (FIG. 6). If the insertion of the putative transmembrane α5, α6-helices of these apoptotic regulators benefits from charge reduction, the lower pH requirement for Bcl-2 may reflect glutamic acid residues that would be prone to ionization with increasing pH in contrast to the presence of lysine and arginine residues in Bax (FIG. 6).

The ion channels formed by Bax and Bcl-2 in planar lipid bilayers have characteristics that depend in part on the method of incorporation. When BaxΔTM or Bcl-2ΔTM is inserted into bilayers at low pH the initial currents were small with conductances of 22 pS and 80 pS respectively.

Like Bcl-x$_L$ (Minn et al., supra), and consistent with other observations on Bcl-2 (Schendel et al, supra), the experiments described herein showed a mild cation selectivity for anti-apoptotic Bcl-2. However, the pro-apoptotic molecule Bax surprisingly has a consistent anion selectivity. If the α5, α6-helices contribute to the channel these selectivities may reflect the positively charged residues of Bax and negatively charged residues of Bcl-2. While modest differences in ion selectivity are unlikely to be the sole explanation for opposite influences on apoptosis, these charge reversals appear to be consistent in the α5, α6-helices of anti- versus pro-apoptotic members (FIG. 7). Bax channels respond to shifting the pH to 7.0 after insertion at pH 4.0 consistent with previous observations on toxins and porins (Mindell et al., *Biophys. J.* 62:41–44, 1992 and Todt et al., Biochem. 31, 10471–10478, 1992). The changes described herein could also relate to pH dependent ionization of charged residues in these channels.

A striking progression of the Bax channel in planar bilayers occurred within 2–4 minutes of its initial appearance. This included i) an early Cl$^−$ selective small channel, ii) a transition phase with multiple subconductance levels and moderate Cl$^−$ selectivity, and iii) an apparently stable ohmic pore of large conductance that is mildly Cl$^−$ selective and open continuously (FIG. 2). The Bcl-2 channel activity also progressed from an early K$^+$ selective small channel that opened and closed spontaneously to a large ohmic pore (FIG. 4). Removal of protein from the chamber and alteration of salt concentrations did not prevent Bax and Bcl-2 channel transition which may represent intra-membranous organization of Bcl-2 or Bax into its mature form. Of note, shifting from pH 4.0 to 7.0 altered the conductance and selectivity of Bax, but not Bcl-2. In contrast, the overnight reconstitution of Bax or Bcl-2 into lipid vesicles which were subsequently fused to planar bilayers resulted immediately in large, open pores (FIGS. 3B and 5C). In addition to differences in ion selectivity, Bcl-2 and Bax channels display other unique characteristics, including conductance, voltage dependence and rectification.

EXAMPLE 8

This example illustrates that the conductance pattern of a Bcl-2 channel is altered by a Bax peptide death agonist (SEQ ID NO:1) to appear similar to that of a Bax channel.

Control bilayers containing Bcl-2 or Bax channels were prepared by fusion of unilamellar proteoliposomes with incorporated Bcl-2ΔTM or BaxΔTM with an established planar bilayer as described in Example 4. Test bilayers containing Bcl-2 channels were prepared in the same manner to which an 11 mer Bax peptide (SEQ ID NO:1) with known death agonist activity was added at 20, 50 or 100 μM. A voltage of 80 mV was applied to each control and test channel and its conductance measured for a period of 12 to 16 seconds and the frequency that each channel was measured at a particular conductance level (pA) was calculated. The data, representing about 500,000 measurements, are shown as histograms in FIGS. 8A–8E.

Figure 8A:
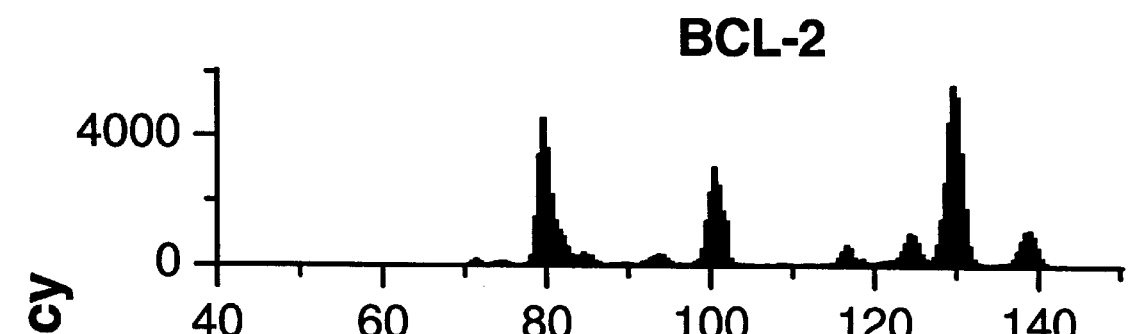
FIGS. 8A–8E illustrates the effect of a death-promoting 11-mer Bax peptide on the conductance characteristics of a Bcl-2 channel in a planar lipid bilayer showing the conductance patterns of Bcl-2 (FIGS. 8A–D) and Bax (FIG. 8E) channels at 80 mV under voltage clamp conditions with the frequency that each channel is present at one of several conductance levels plotted against the conductance in pico-amps in the absence (FIGS. 8A and 8E) or presence of the 11mer peptide at 20 μM (FIG. 8B), 50 μM (FIG. 8C), or 100 μM (FIG. 8D)

As seen in FIG. 8A, the Bcl-2 control channel moves between several conductance levels, clustering around preferred open states at about 80 pA, 102 pA, and 130 pA. Bax displays a simpler conductance pattern, with two preferred conductance levels between about 45 and 55 pA (FIG. 8E).

Figure 8B:
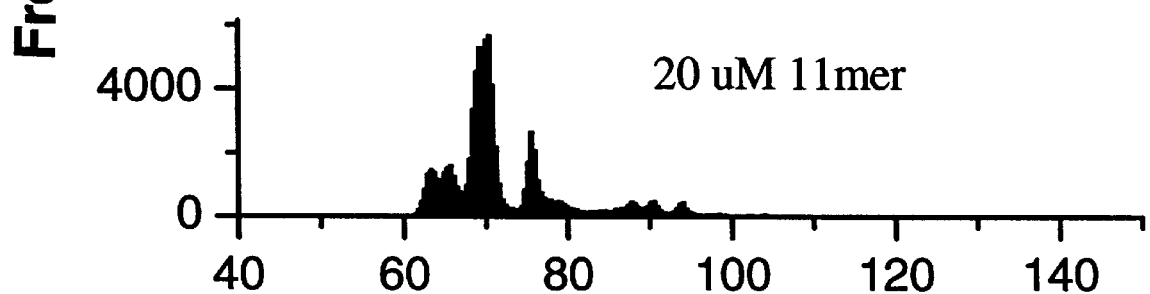
Figure 8C:
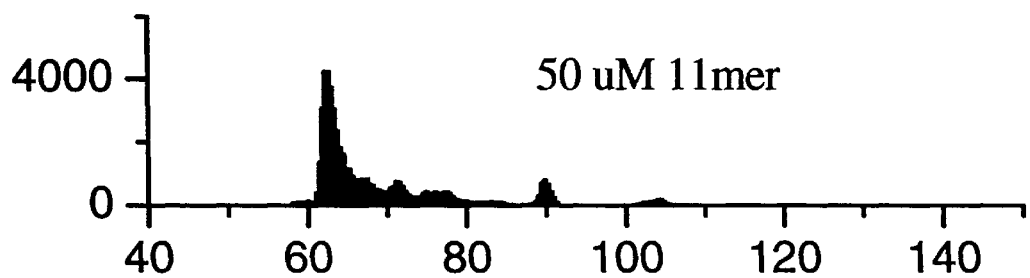
Figure 8D:
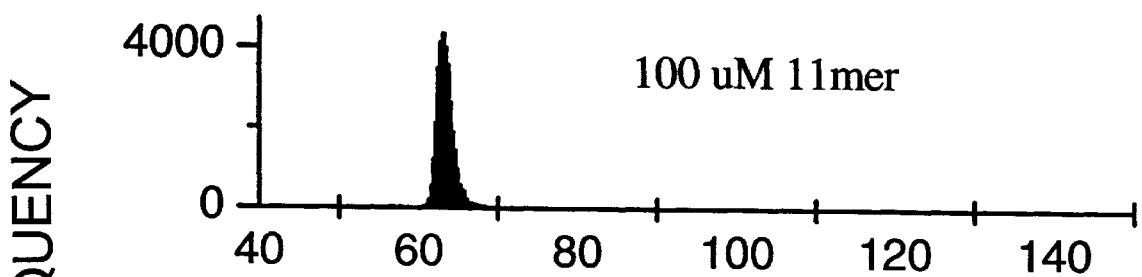
Figure 8E:
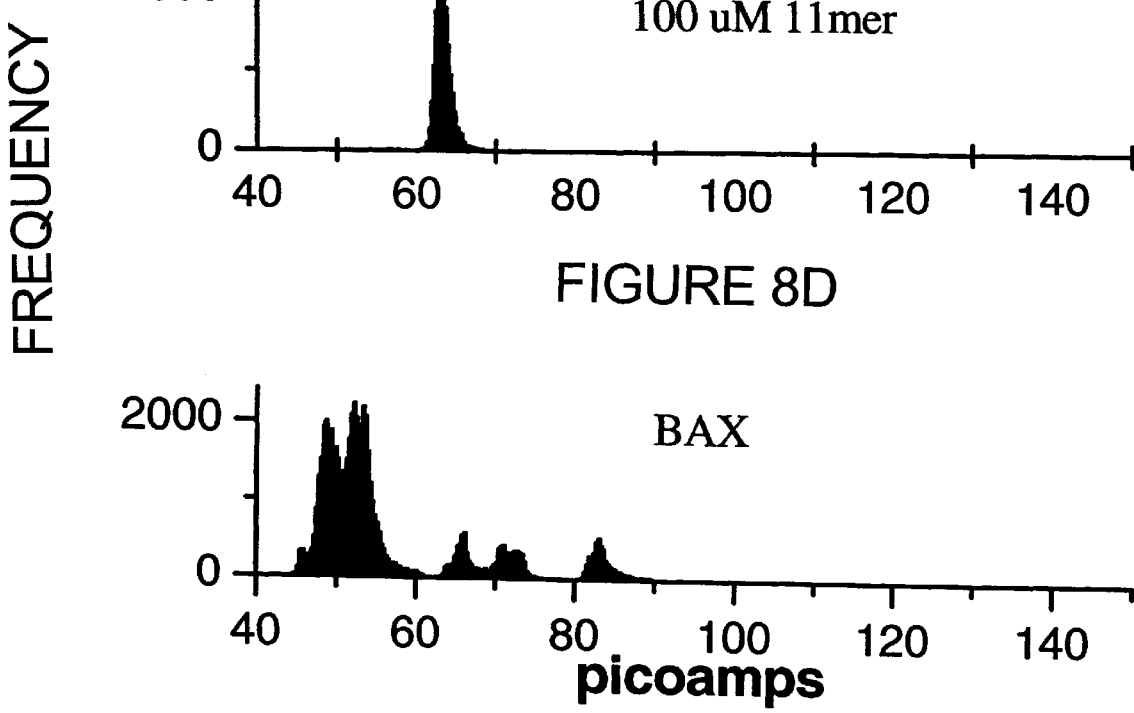

The addition of the 11 mer Bax peptide to a Bcl-2 channel changes its characteristic conductance pattern in a progressive manner as the concentration is increased from 20 to 100 μM (FIGS. 8B–D). At 100 μM the single remaining peak is not coincident with any of the levels seen in Bcl-2 but coincides with one of the less frequent Bax peaks at about 65 pA. When murine T cell hybridoma 2B4 cells are treated with 100 μM of this peptide fused with the HIV tat peptide, which increases cell uptake of the Bax peptide, a significant number of the cells are dead in less than 4 hr as compared to treatment with the tat peptide alone (data not shown). Thus, the complex conductance pattern of a Bcl-2 channel is altered to a simpler Bax-like conductance pattern by the same concentration of peptide that promotes cell death in vitro.

The activity of Bax channels in the lipid bilayer was not affected by addition of the Bax 11-mer peptide at concentrations between 20 and 100 μM. In addition, the Bax 1-mer peptide exhibited no channel forming activity upon addition to planar lipid bilayers which lack BCL-2 related proteins.

EXAMPLE 9

This example illustrates the effect of the Bax death agonist peptide on ion selectivity and conductance of a Bcl-2 channel.

Figure 9A:
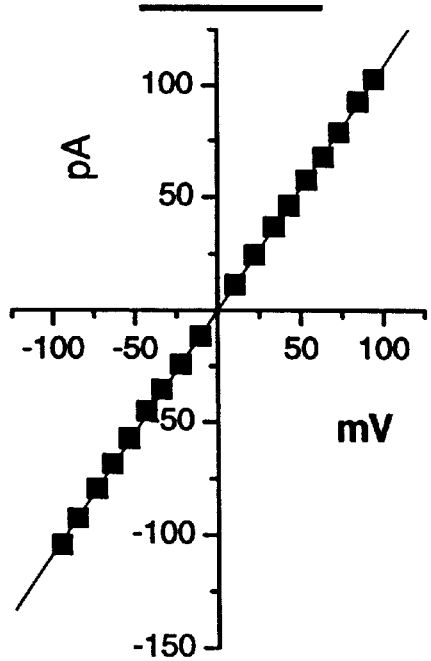
FIGS. 9A–9C illustrates the effect of the Bax death agonist peptide on the conductance and ion selectivity of a Bcl-2 channel showing an IV plot of channel activity at 150 mM symmetrical KCl and the pK/pCl calculated from the reversal potential in a 450:150 mM cis:trans KCl gradient for (FIG. 9A) a Bcl-2 channel, (FIG. 9B) a Bcl-2 channel after the addition of the Bax death agonist peptide to the cis side of the bilayer, and (FIG. 9C) a Bax channel, with the slope of the conductance at negative potentials indicated.

Bilayers containing Bcl-2 and Bax channels were prepared as described in Example 4 with 150 mM KCl on both sides of the bilayer. The death agonist peptide was added to the cis side of a Bcl-2 channel at 150 μM. The voltage dependence of the currents and the ion selectivity for the Bcl-2 channel in the absence and presence of the death agonist peptide, as well as the Bax channel were determined and the data are shown in FIGS. 9A–C.

Figure 9B:
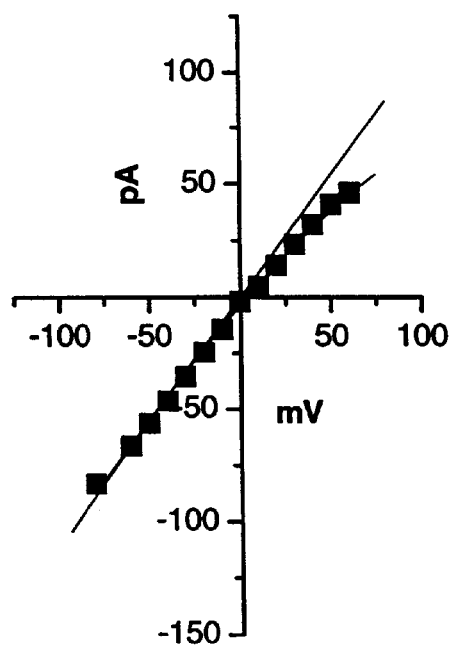
Figure 9C:
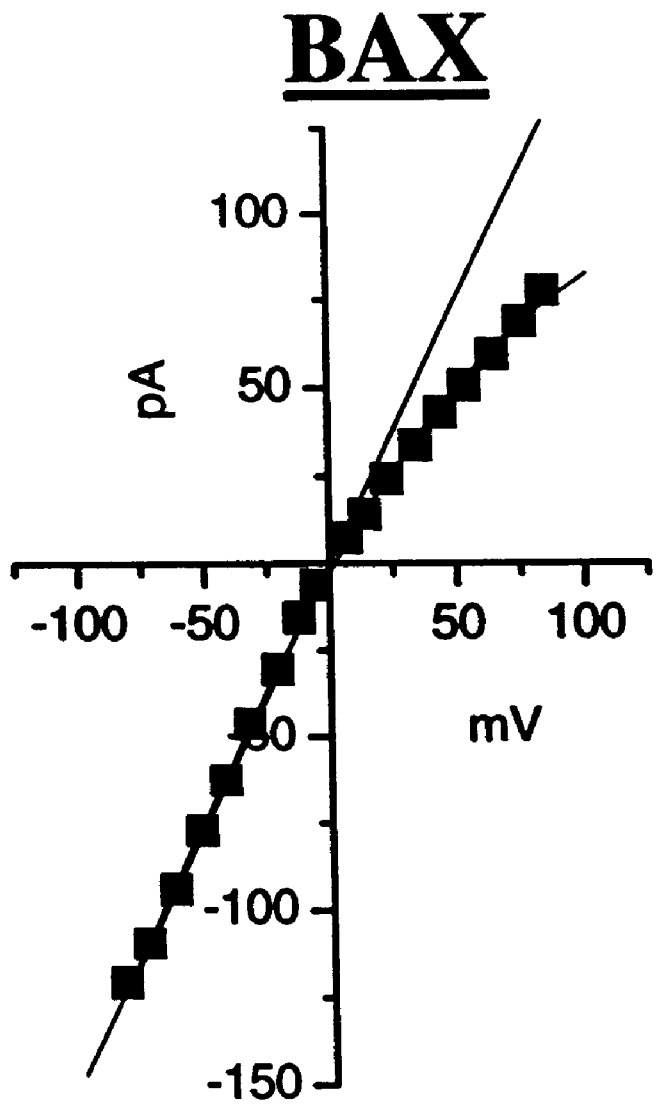

The IV plots show that the death agonist peptide imparted rectification to the voltage dependence of the Bcl-2 channel current, similar to the rectification displayed by the Bax channel, as indicated by the curving lines at positive potentials in the plots in FIGS. 9B and 9C. The slope of Bcl-2 channels in the presence of the death agonist peptide and at negative potentials is linear and intermediate between that of Bcl-2 and Bax alone. Of note, addition of the death agonist peptide reversed the ion selectivity of the Bcl-2 channel from $K^+$ selective with a pK/pCl=2.4) to Cl– selective with a pK/pCl value, 0.26±0.05, within the range of that measured for the Bax channel (0.32 pK/pCl).

In summary, the experiments described above show that the characteristic activity of a Bcl-2 channel is altered in the presence of a peptide which promotes cell death in vitro to appear more similar to the activity of a Bax channel.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification either supra or infra are hereby incorporated by reference. The discussion of the references herein is intended merely to summarize the assertions made by their authors and no admission is made as to the accuracy or pertinency of the references or that any reference is material to patentability.

What is claimed is:

1. A method for identifying apoptosis-modulating compounds which comprises:
   (a) providing a lipid bilayer that includes a $K^+$- or an $Cl^-$-selective channel wherein the covel comprises anti-apoptotic or pro-apoptotic polypeptide of the BCL-2 family, respectively, or fragment thereof which is capable of forming an ion selective channel in vitro;
   (b) contacting a compound of interest with the bilayer; and
   (c) determining ion-selectivity of the channel wherein a change from $K^+$-selective to $Cl^-$-selective indicates the compound is a death agonist and a change from $Cl^-$-selective to $K^+$-selective indicates the compound is a death antagonist.

2. The method of claim 1, wherein the channel comprises an anti-apoptotic polypeptide of the BCL-2 family.

3. The method of claim 2, wherein the anti-apoptotic polypeptide is Bcl-2ΔTM.

4. The method of claim 2, wherein the lipid bilayer comprises a proteoliposome loaded with a mixture of $K^+$ and $Cl^-$ in known amounts and wherein determining ion selectivity comprises measuring the relative rates of $K^+$ and $Cl^-$ efflux from the proteoliposome.

5. The method of claim 4, wherein the anti-apoptotic polypeptide is Bcl-2ΔTM.

6. The method of claim 2, wherein the lipid bilayer comprises a planar bilayer in the presence of an ion concentration gradient and the determining ion selectivity step comprises measuring the reversal potential of the channel.

7. The method of claim 1, wherein the channel comprises a pro-apoptotic polypeptide of the BCL-2 family.

8. The method of claim 7, wherein the pro-apoptotic polypeptide is BaxΔTM.

9. The method of claim 7, wherein the lipid bilayer comprises a planar bilayer in the presence of an ion concentration gradient and the determining ion selectivity step comprises measuring the reversal potential of the channel.

10. The method of claim 7, wherein the lipid bilayer comprises a proteoliposome loaded with a mixture of $K^+$ and $Cl^-$ in known amounts and wherein determining ion selectivity comprises measuring the relative rates of $K^+$ and $Cl^-$ efflux from the proteoliposome.

* * * * *

UNITED STATES PATENT AND TRADEMARK OFFICE
CERTIFICATE OF CORRECTION

PATENT NO. : 6,165,732
DATED : December 26, 2000
INVENTOR(S) : Korsmeyer et al.

Page 1 of 1

It is certified that error appears in the above-identified patent and that said Letters Patent is hereby corrected as shown below:

Figure 11, Mouse Bax sequence, replace "P" at position 8 with -- L --;
replace "R" at position 9 with -- G --;
replace "G" at position 10 with -- S --;
replace "L" at position 25 with -- F --;
replace "G" at position 39 with -- A --;
replace "A" at position 42 with -- T --;
replace "A" at position 46 with -- T --;
replace "D" at position 48 with -- E --;
replace "P" at position 49 with -- Q --;
replace "V" at position 50 with -- P --;
replace "K" at position 64 with -- R --;
replace "A" at position 82 with -- D --;
replace "S" at position 101 with -- A --;
replace "D" at position 159 with -- E --.

Figure 11, Human Bcl-2 sequence, replace "C" at position 129 with -- R --.
Mouse Bcl-2 sequence, replace "C" at position 98 with -- G --.

Specifications,
Column 6,
Lines 37-40, after (SEQ ID NOS: 8-9) delete ", with identical residues and conservative substitutions shaded dark and light, respectively, exon boundaries indicated by vertical dashed lines, and the BH1 and BH2 domains boxed"

Claims
Claim 1,
Line 4, replace "covel" with -- channel --.

Signed and Sealed this

Twenty-third Day of October, 2001

Attest:

*Nicholas P. Godici*

NICHOLAS P. GODICI
*Attesting Officer*   *Acting Director of the United States Patent and Trademark Office*

SEQUENCE LISTING

<160> NUMBER OF SEQ ID NOS: 9

<210> SEQ ID NO 1
<211> LENGTH: 11
<212> TYPE: PRT
<213> ORGANISM: mammalian

<400> SEQUENCE: 1

Glu Cys Leu Lys Arg Ile Gly Asp Glu Leu Asp
 1               5                  10

<210> SEQ ID NO 2
<211> LENGTH: 51
<212> TYPE: PRT
<213> ORGANISM: mammalian

<400> SEQUENCE: 2

Val Asn Trp Gly Arg Ile Val Ala Phe Phe Ser Phe Gly Gly Ala Leu
 1               5                  10                  15

Cys Val Glu Ser Val Asp Lys Glu Met Gln Val Leu Val Ser Arg Ile
            20                  25                  30

Ala Ala Trp Met Ala Thr Tyr Leu Asn Asp His Leu Glu Pro Trp Ile
        35                  40                  45

Gln Glu Asn
    50

<210> SEQ ID NO 3
<211> LENGTH: 51
<212> TYPE: PRT
<213> ORGANISM: mammalian

-continued

```
<400> SEQUENCE: 3

Val Asn Trp Gly Arg Ile Val Ala Phe Phe Glu Phe Gly Gly Val Met
 1               5                  10                  15

Cys Val Glu Ser Val Asn Arg Glu Met Ser Pro Leu Val Asp Asn Ile
            20                  25                  30

Ala Leu Trp Met Thr Glu Tyr Leu Asn Arg His Leu His Thr Trp Ile
        35                  40                  45

Gln Asp Asn
    50

<210> SEQ ID NO 4
<211> LENGTH: 51
<212> TYPE: PRT
<213> ORGANISM: mammalian

<400> SEQUENCE: 4

Phe Asn Trp Gly Arg Val Val Ala Leu Phe Tyr Phe Ala Ser Lys Leu
 1               5                  10                  15

Val Lys Leu Ala Leu Cys Thr Lys Val Pro Glu Leu Ile Arg Thr Ile
            20                  25                  30

Met Gly Trp Thr Leu Asp Phe Leu Arg Glu Arg Leu Leu Gly Trp Ile
        35                  40                  45

Gln Asp Gln
    50

<210> SEQ ID NO 5
<211> LENGTH: 52
<212> TYPE: PRT
<213> ORGANISM: mammalian

<400> SEQUENCE: 5

Ile Asn Trp Gly Arg Val Val Ala Leu Leu Gly Phe Gly Tyr Arg Leu
 1               5                  10                  15

Ala Leu His Val Tyr Gln His Gly Leu Thr Gly Phe Leu Gly Gln Val
            20                  25                  30

Thr Arg Phe Val Val Asp Phe Met Leu His His Cys Ile Ala Arg Trp
        35                  40                  45

Ile Ala Gln Arg
    50

<210> SEQ ID NO 6
<211> LENGTH: 192
<212> TYPE: PRT
<213> ORGANISM: Mouse

<400> SEQUENCE: 6

Met Asp Gly Ser Gly Glu Gln Leu Gly Ser Gly Gly Pro Thr Ser Ser
 1               5                  10                  15

Glu Gln Ile Met Lys Thr Gly Ala Phe Leu Leu Gln Gly Phe Ile Gln
            20                  25                  30

Asp Arg Ala Gly Arg Met Ala Gly Glu Thr Pro Glu Leu Thr Leu Glu
        35                  40                  45

Gln Pro Pro Gln Asp Ala Ser Thr Lys Lys Leu Ser Glu Cys Leu Arg
    50                  55                  60

Arg Ile Gly Asp Glu Leu Asp Ser Asn Met Glu Leu Gln Arg Met Ile
 65                  70                  75                  80

Ala Asp Val Asp Thr Asp Ser Pro Arg Glu Val Phe Phe Arg Val Ala
                85                  90                  95
```

```
Ala Asp Met Phe Ala Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Val Trp Ile Gln Asp Gln Gly Trp Glu Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 7
<211> LENGTH: 192
<212> TYPE: PRT
<213> ORGANISM: Homo sapiens

<400> SEQUENCE: 7

Met Asp Gly Ser Gly Glu Gln Pro Arg Gly Gly Pro Thr Ser Ser
  1               5                  10                  15

Glu Gln Ile Met Lys Thr Gly Ala Leu Leu Leu Gln Gly Phe Ile Gln
             20                  25                  30

Asp Arg Ala Gly Arg Met Gly Gly Glu Ala Pro Glu Leu Ala Leu Asp
         35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
 65                  70                  75                  80

Ala Ala Val Asp Thr Asp Ser Pro Arg Glu Val Phe Phe Arg Val Ala
                 85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 8
<211> LENGTH: 239
<212> TYPE: PRT
<213> ORGANISM: Homo sapiens

<400> SEQUENCE: 8

Met Ala His Ala Gly Arg Thr Gly Tyr Asp Asn Arg Glu Ile Val Met
  1               5                  10                  15

Lys Tyr Ile His Tyr Lys Leu Ser Gln Arg Gly Tyr Glu Trp Asp Ala
             20                  25                  30

Gly Asp Val Gly Ala Ala Pro Pro Gly Ala Ala Pro Ala Pro Gly Ile
         35                  40                  45
```

-continued

Phe Ser Ser Gln Pro Gly His Thr Pro His Pro Ala Ala Ser Arg Asp
 50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Pro Val Val His Leu Thr
                 85                  90                  95

Leu Arg Gln Ala Gly Asp Asp Phe Ser Arg Tyr Arg Arg Asp Phe
                100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
        130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 9
<211> LENGTH: 236
<212> TYPE: PRT
<213> ORGANISM: Mouse

<400> SEQUENCE: 9

Met Ala Gln Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
            20                  25                  30

Gly Asp Ala Asp Ala Ala Pro Leu Gly Ala Ala Pro Thr Pro Gly Ile
        35                  40                  45

Phe Ser Phe Gln Pro Glu Ser Asn Pro Met Pro Ala Val His Arg Glu
 50                  55                  60

Met Ala Ala Arg Thr Ser Pro Leu Arg Pro Leu Val Ala Thr Ala Gly
 65                  70                  75                  80

Pro Ala Leu Ser Pro Val Pro Pro Cys Val His Leu Thr Leu Arg Arg
                 85                  90                  95

Ala Gly Asp Asp Phe Ser Arg Arg Tyr Arg Arg Asp Phe Ala Glu Met
                100                 105                 110

Ser Ser Gln Leu His Leu Thr Pro Phe Thr Ala Arg Gly Arg Phe Ala
            115                 120                 125

Thr Val Val Glu Glu Leu Phe Arg Asp Gly Val Asn Trp Gly Arg Ile
        130                 135                 140

Val Ala Phe Phe Glu Phe Gly Gly Val Met Cys Val Glu Ser Val Asn
145                 150                 155                 160

Arg Glu Met Ser Pro Leu Val Asp Asn Ile Ala Leu Trp Met Thr Glu
                165                 170                 175

Tyr Leu Asn Arg His Leu His Thr Trp Ile Gln Asp Asn Gly Gly Trp

-continued

```
            180                 185                 190
Asp Ala Phe Val Glu Leu Tyr Gly Pro Ser Met Arg Pro Leu Phe Asp
        195                 200                 205
Phe Ser Trp Leu Ser Leu Lys Thr Leu Leu Ser Leu Ala Leu Val Gly
    210                 215                 220
Ala Cys Ile Thr Leu Gly Ala Tyr Leu Gly His Lys
225                 230                 235
```